United States Patent
Ori

(10) Patent No.: US 9,949,663 B1
(45) Date of Patent: Apr. 24, 2018

(54) APPARATUS AND METHOD FOR THE ANALYSIS OF THE CHANGE OF BODY COMPOSITION AND HYDRATION STATUS AND FOR DYNAMIC INDIRECT INDIVIDUALIZED MEASUREMENT OF COMPONENTS OF THE HUMAN ENERGY METABOLISM

(71) Applicant: Zsolt Peter Ori, Durham, NC (US)

(72) Inventor: Zsolt Peter Ori, Durham, NC (US)

(73) Assignee: ORI DIAGNOSTIC INSTRUMENTS, LLC, Durham, NC (US)

( * ) Notice: Subject to any disclaimer, the term of this patent is extended or adjusted under 35 U.S.C. 154(b) by 261 days.

(21) Appl. No.: 14/541,033

(22) Filed: Nov. 13, 2014

(51) Int. Cl.
*A61B 5/05* (2006.01)
*A61B 5/053* (2006.01)
(Continued)

(52) U.S. Cl.
CPC .......... *A61B 5/0537* (2013.01); *A61B 5/4872* (2013.01); *A61B 5/4875* (2013.01); *A61B 5/7278* (2013.01); *G06F 19/24* (2013.01)

(58) Field of Classification Search
None
See application file for complete search history.

(56) References Cited

U.S. PATENT DOCUMENTS

| 5,280,429 A | 1/1994 | Withers |
| 6,506,152 B1 | 1/2003 | Lackey |

(Continued)

OTHER PUBLICATIONS

Kevin D. Hall, Computational model of in vivo human energy metabolism during semistarvation and refeeding. Am. J. Physiol. Endocrinol. Metab. 291: E23-E37, 2006. Jan. 31, 2006; doi:10.1152/ajpendo.00523.2005.

(Continued)

*Primary Examiner* — Devin Henson
*Assistant Examiner* — Benjamin Melhus
(74) *Attorney, Agent, or Firm* — Olive Law Group, PLLC

(57) ABSTRACT

One embodiment of an apparatus for analysis of body composition and hydration status by detecting resistance of the human subject at zero and infinite frequency including a method for measuring indirectly extracellular water mass, intracellular water mass, lean body mass, and body fat mass; daily changes of extracellular water mass, intracellular water mass, lean body mass, and body fat mass; and acute changes of extracellular water mass and intracellular water mass; and for individualized calibration of these indirect measurements.

Figure 1:
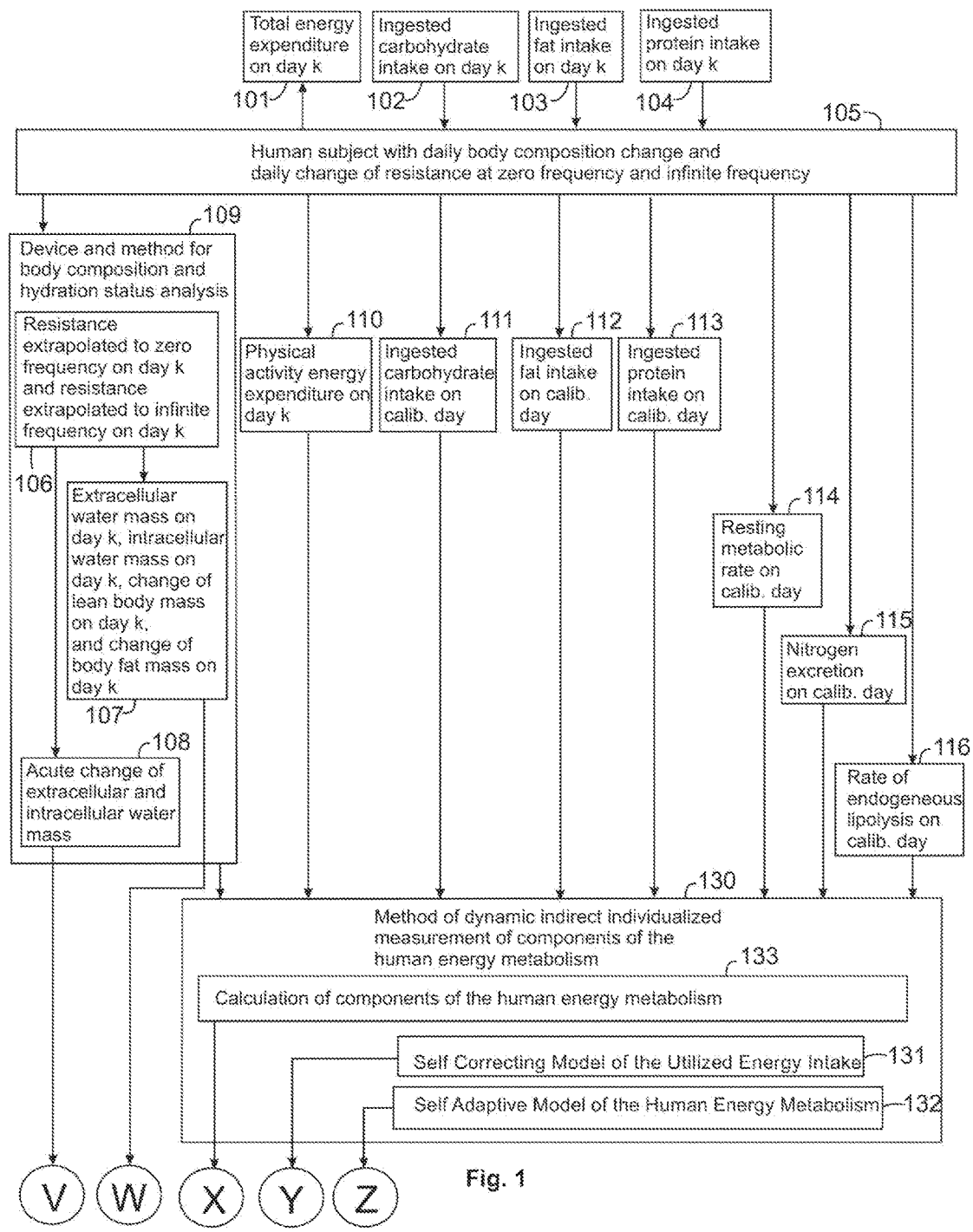
Figure 1A:
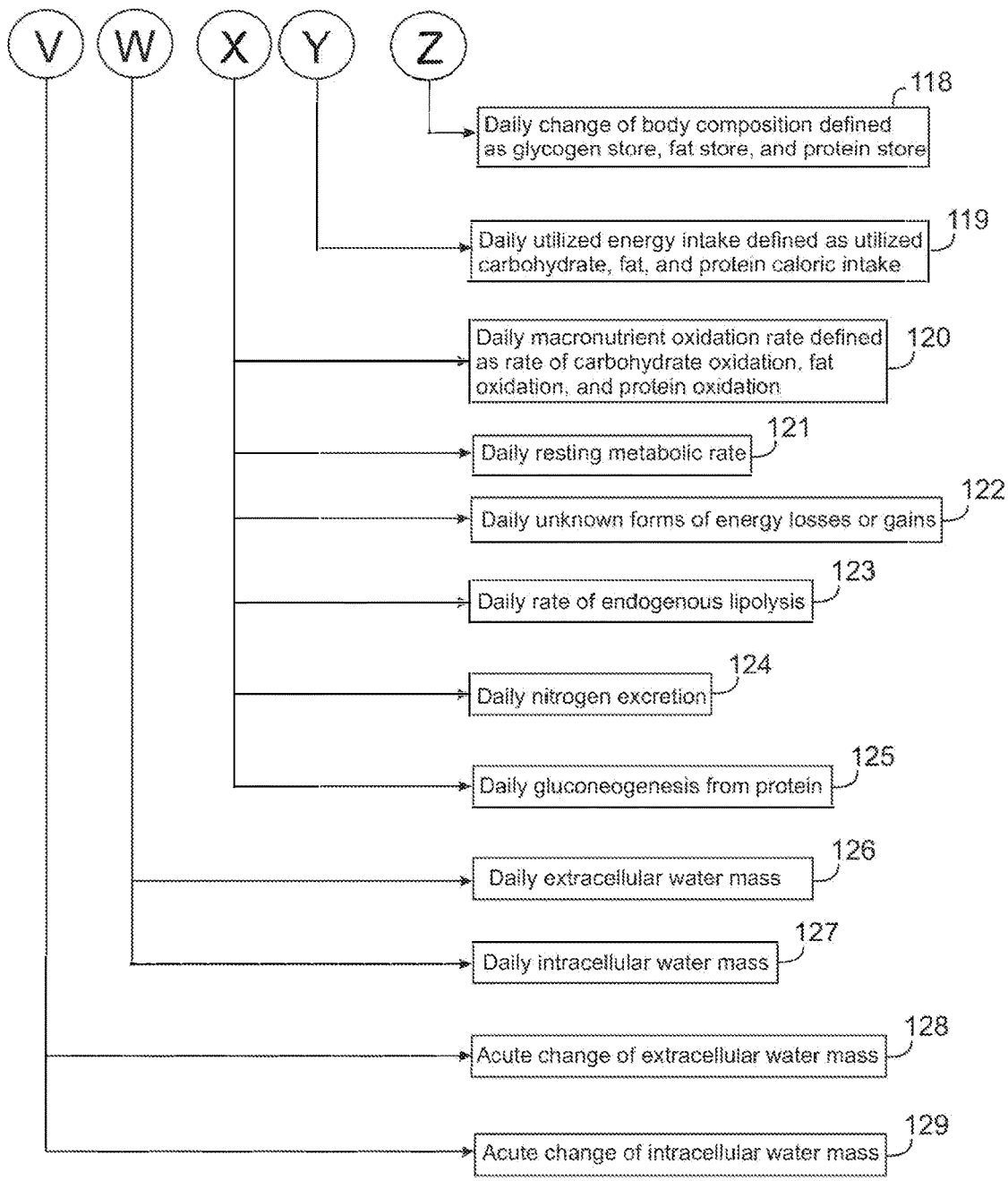

In addition, a method for fitting mathematical models to serial measurements of indirectly measured lean body mass and fat mass and for dynamic indirect individualized measurement using minimum variance estimation and prediction of daily changes of the body composition defined as change of glycogen store, change of fat store and change of protein store; daily utilized macronutrient energy intake defined as utilized carbohydrate, fat, and protein caloric intake; daily macronutrient oxidation rate defined as rate of carbohydrate oxidation, fat oxidation, and protein oxidation; daily resting metabolic rate; daily unknown forms of energy losses or gains; daily rate of endogenous lipolysis; daily nitrogen excretion; daily gluconeogenesis from protein; daily determination of extracellular water mass; daily determination of intracellular water mass; and acute change of extracellular water mass and intracellular water mass.

14 Claims, 20 Drawing Sheets

(51) Int. Cl.
*A61B 5/00* (2006.01)
*G06F 19/24* (2011.01)

(56) References Cited

U.S. PATENT DOCUMENTS

| | | |
|---|---|---|
| 6,620,106 B2 | 9/2003 | Mault |
| 6,694,182 B1* | 2/2004 | Yamazaki .......... A61B 5/02438 600/547 |
| 87,129 A1 | 4/2011 | Chetham |
| 2004/0133081 A1* | 7/2004 | Teller .................. A61B 5/01 600/300 |

OTHER PUBLICATIONS

Kevin D. Hall, Predicting metabolic adaptation, body weight change, and energy intake in humans. Am. J. Physiol. Endocrinol. Metab. 298: E449-E466, 2010. Nov. 24, 2009; doi:10.1152/ajpendo.00559.2009.

Ulrich M. Moissl, Body fluid volume determination via body composition spectroscopy in health and disease. Physiol. Meas. 27 (2006) 921-933. Jul. 25, 2006; doi:10.1088/0967-3334/27/9/012.

* cited by examiner

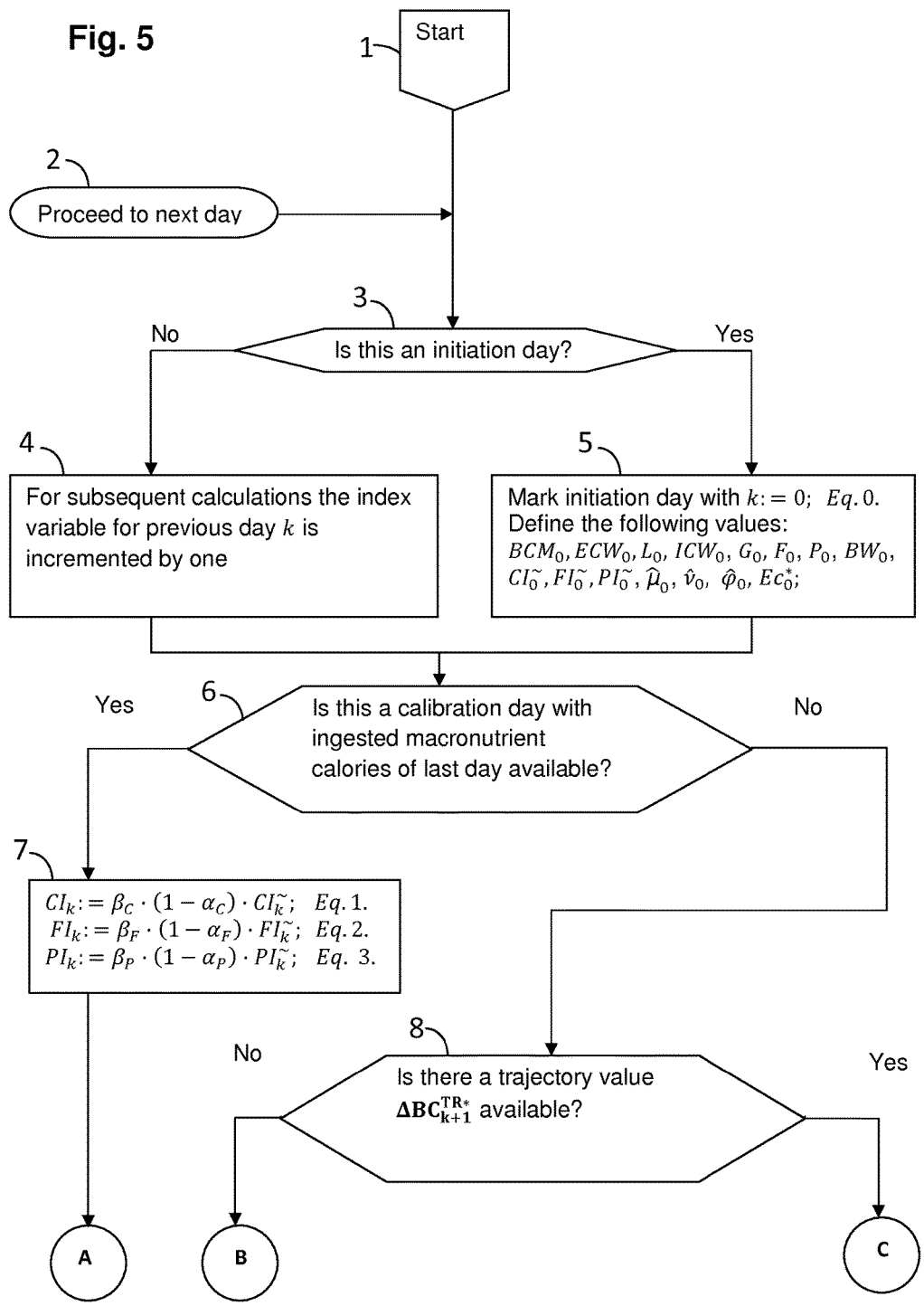

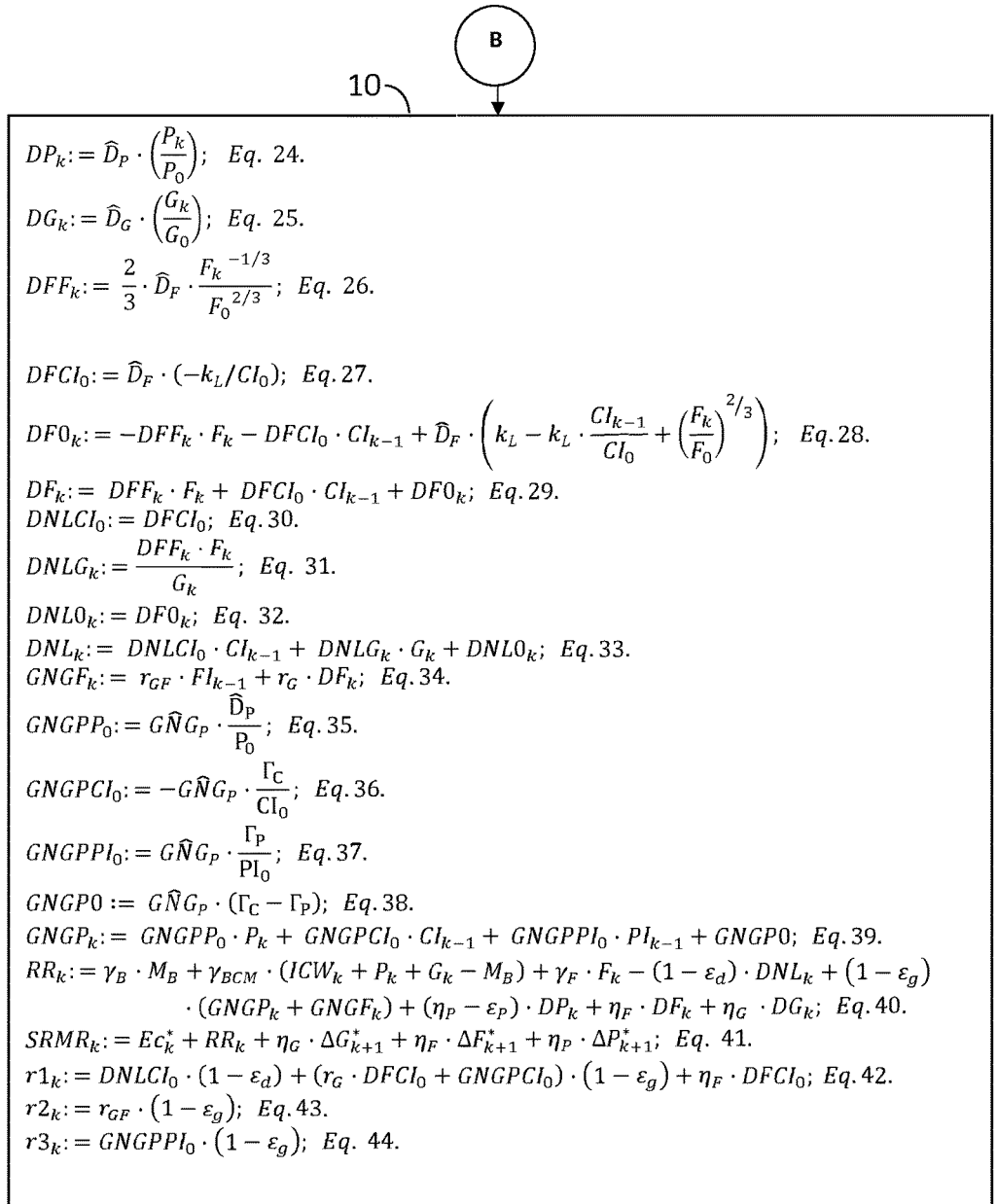

$$DP_k := \hat{D}_P \cdot \left(\frac{P_k}{P_0}\right); \quad Eq.\ 24.$$

$$DG_k := \hat{D}_G \cdot \left(\frac{G_k}{G_0}\right); \quad Eq.\ 25.$$

$$DFF_k := \frac{2}{3} \cdot \hat{D}_F \cdot \frac{F_k^{-1/3}}{F_0^{2/3}}; \quad Eq.\ 26.$$

$$DFCI_0 := \hat{D}_F \cdot (-k_L/CI_0); \quad Eq.\ 27.$$

$$DF0_k := -DFF_k \cdot F_k - DFCI_0 \cdot CI_{k-1} + \hat{D}_F \cdot \left(k_L - k_L \cdot \frac{CI_{k-1}}{CI_0} + \left(\frac{F_k}{F_0}\right)^{2/3}\right); \quad Eq.\ 28.$$

$$DF_k := DFF_k \cdot F_k + DFCI_0 \cdot CI_{k-1} + DF0_k; \quad Eq.\ 29.$$

$$DNLCI_0 := DFCI_0; \quad Eq.\ 30.$$

$$DNLG_k := \frac{DFF_k \cdot F_k}{G_k}; \quad Eq.\ 31.$$

$$DNL0_k := DF0_k; \quad Eq.\ 32.$$

$$DNL_k := DNLCI_0 \cdot CI_{k-1} + DNLG_k \cdot G_k + DNL0_k; \quad Eq.\ 33.$$

$$GNGF_k := r_{GF} \cdot FI_{k-1} + r_G \cdot DF_k; \quad Eq.\ 34.$$

$$GNGPP_0 := G\hat{N}G_P \cdot \frac{\hat{D}_P}{P_0}; \quad Eq.\ 35.$$

$$GNGPCI_0 := -G\hat{N}G_P \cdot \frac{\Gamma_C}{CI_0}; \quad Eq.\ 36.$$

$$GNGPPI_0 := G\hat{N}G_P \cdot \frac{\Gamma_P}{PI_0}; \quad Eq.\ 37.$$

$$GNGP0 := G\hat{N}G_P \cdot (\Gamma_C - \Gamma_P); \quad Eq.\ 38.$$

$$GNGP_k := GNGPP_0 \cdot P_k + GNGPCI_0 \cdot CI_{k-1} + GNGPPI_0 \cdot PI_{k-1} + GNGP0; \quad Eq.\ 39.$$

$$RR_k := \gamma_B \cdot M_B + \gamma_{BCM} \cdot (ICW_k + P_k + G_k - M_B) + \gamma_F \cdot F_k - (1 - \varepsilon_d) \cdot DNL_k + (1 - \varepsilon_g) \cdot (GNGP_k + GNGF_k) + (\eta_P - \varepsilon_P) \cdot DP_k + \eta_F \cdot DF_k + \eta_G \cdot DG_k; \quad Eq.\ 40.$$

$$SRMR_k := Ec_k^* + RR_k + \eta_G \cdot \Delta G_{k+1}^* + \eta_F \cdot \Delta F_{k+1}^* + \eta_P \cdot \Delta P_{k+1}^*; \quad Eq.\ 41.$$

$$r1_k := DNLCI_0 \cdot (1 - \varepsilon_d) + (r_G \cdot DFCI_0 + GNGPCI_0) \cdot (1 - \varepsilon_g) + \eta_F \cdot DFCI_0; \quad Eq.\ 42.$$

$$r2_k := r_{GF} \cdot (1 - \varepsilon_g); \quad Eq.\ 43.$$

$$r3_k := GNGPPI_0 \cdot (1 - \varepsilon_g); \quad Eq.\ 44.$$

FIG. 5B

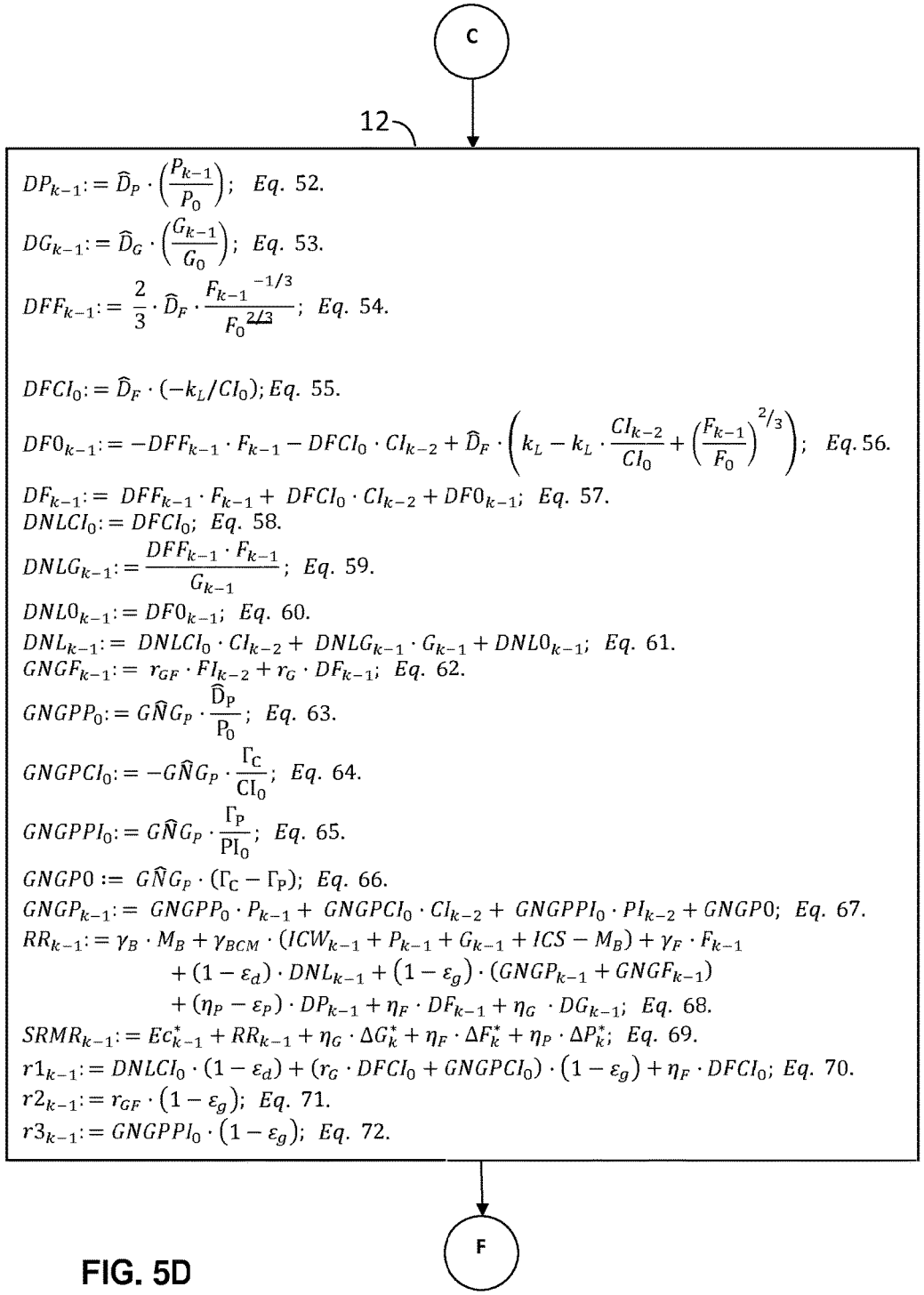

Figure 5A:
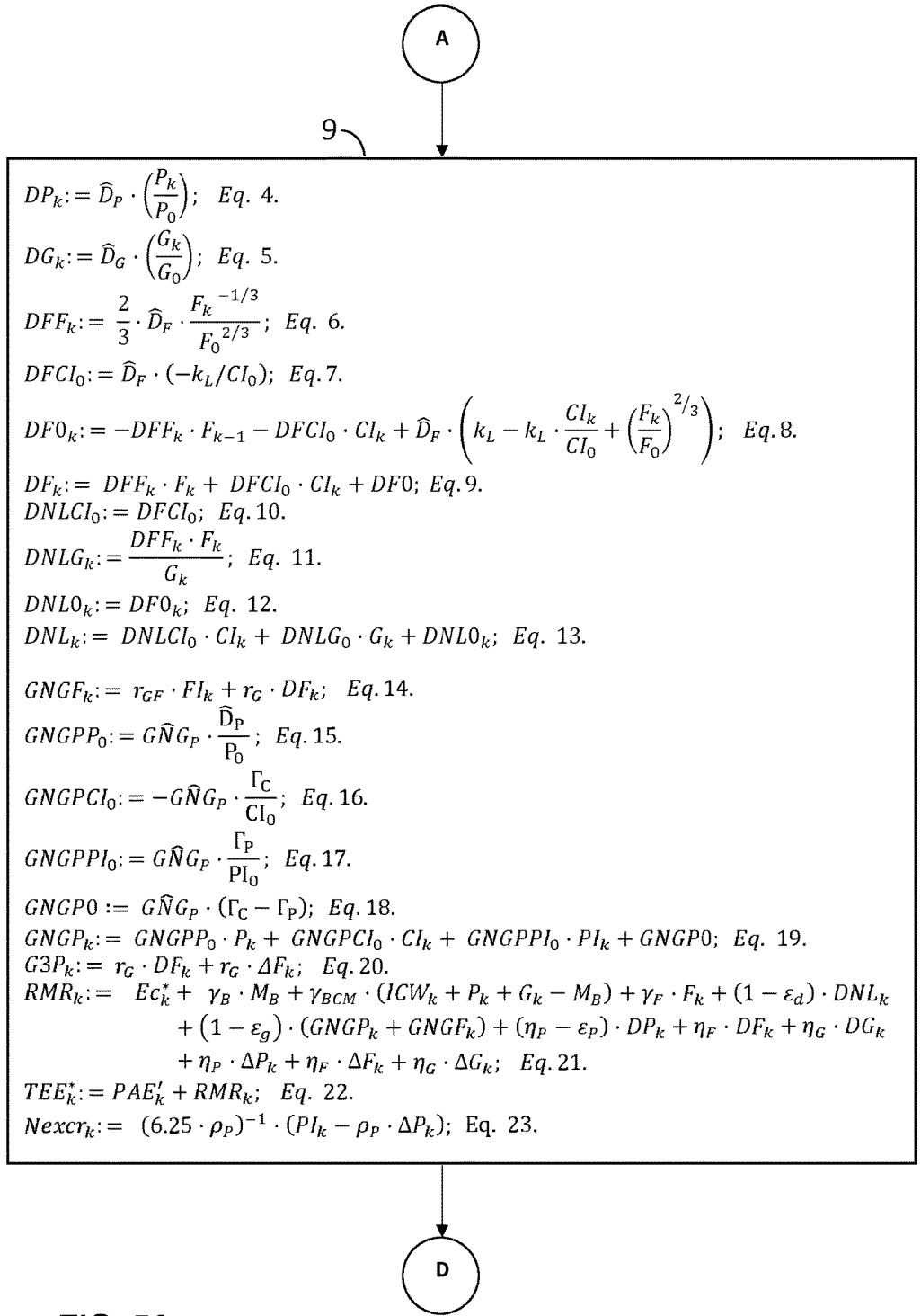
Figure 5C:
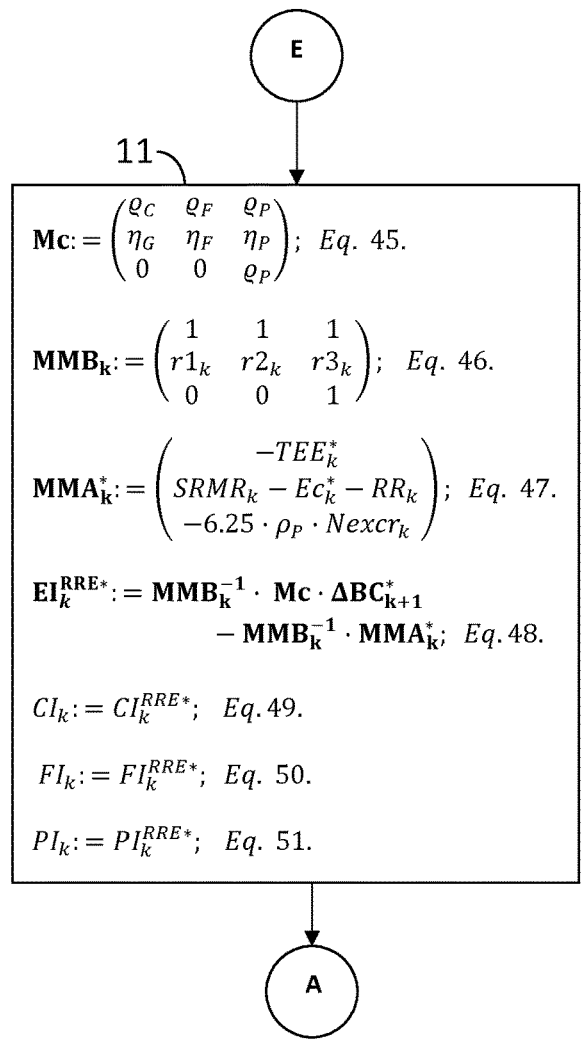
Figure 5G:
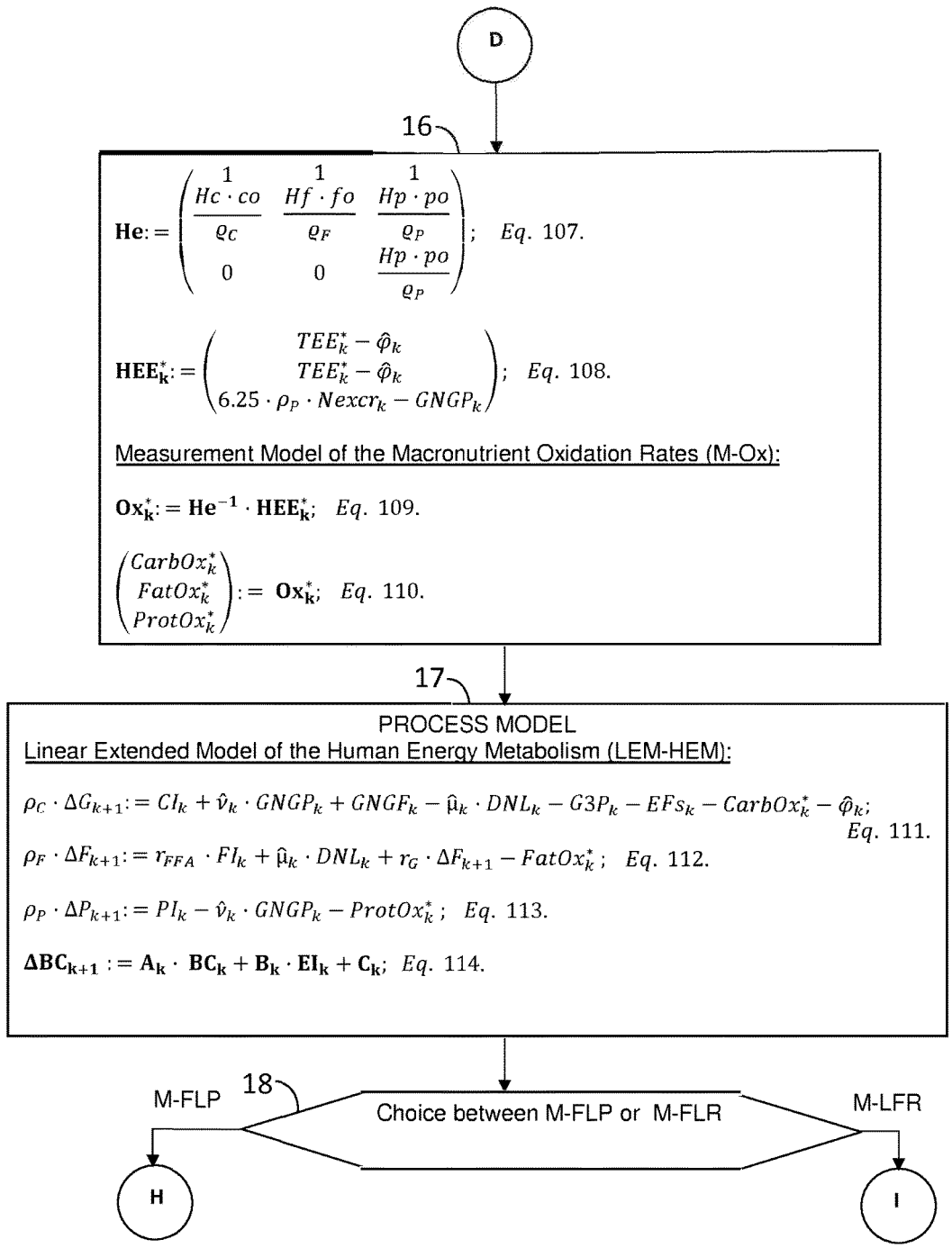
Figure 5H:
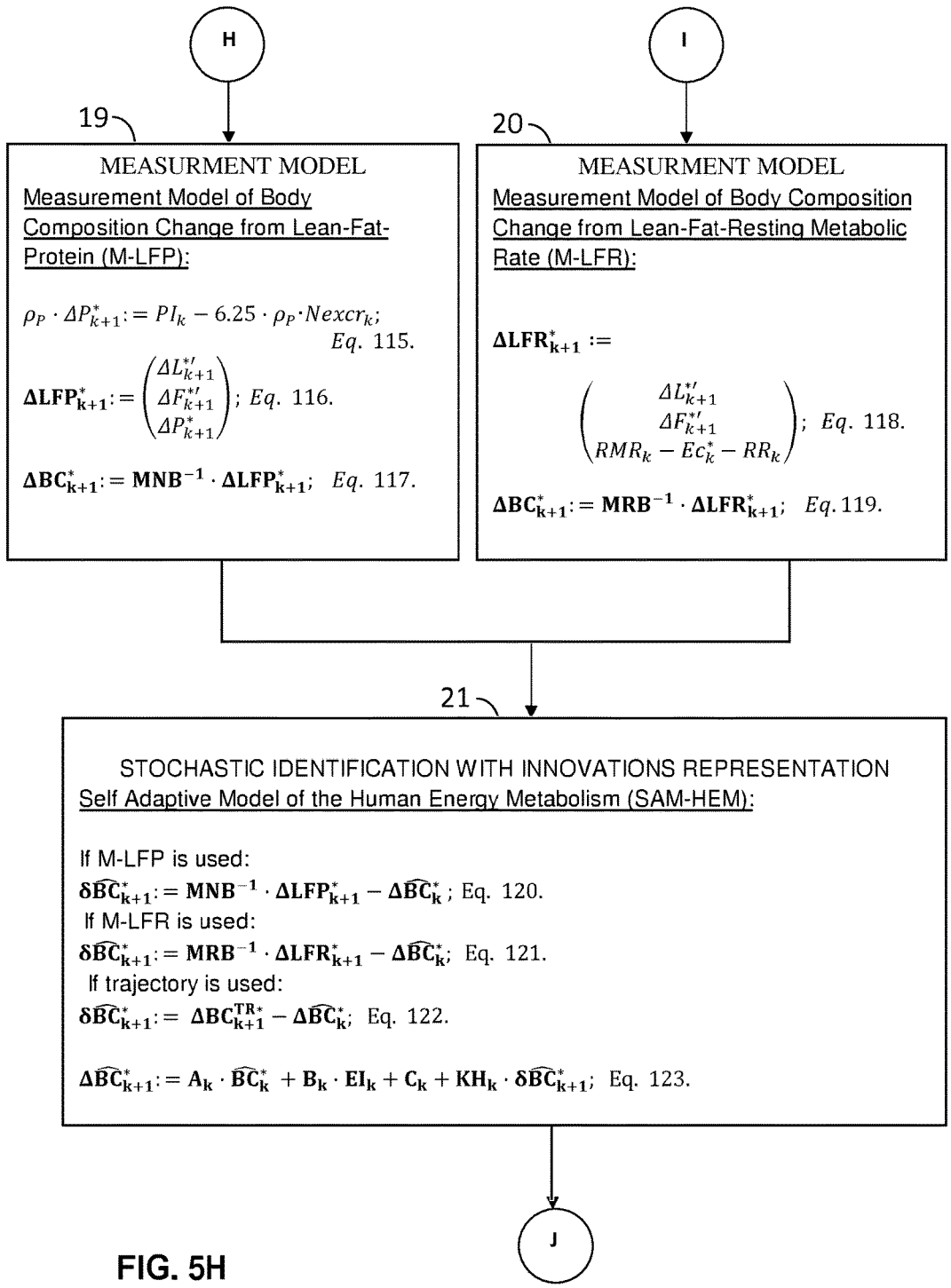
Figure 5I:
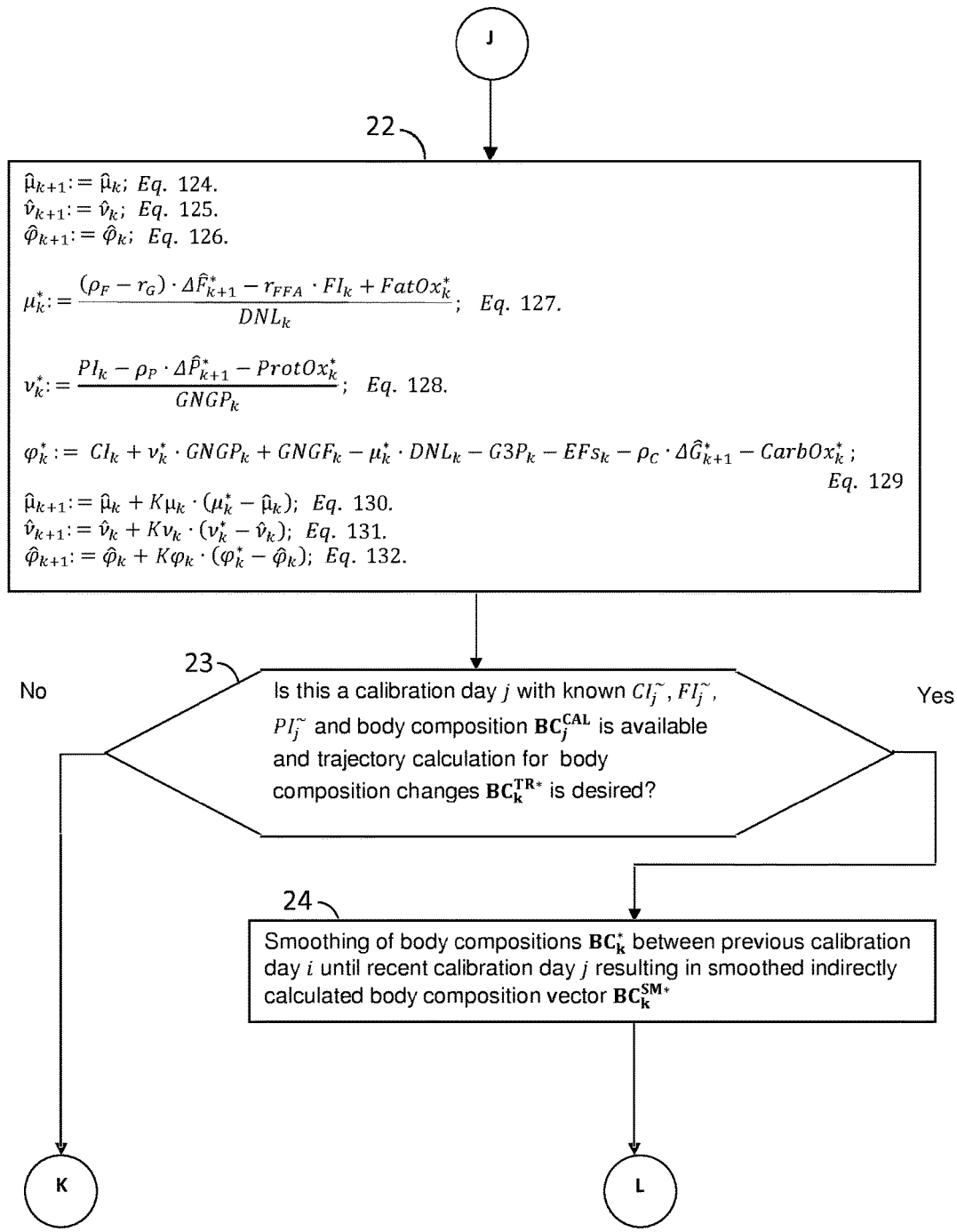
Figure 5J:
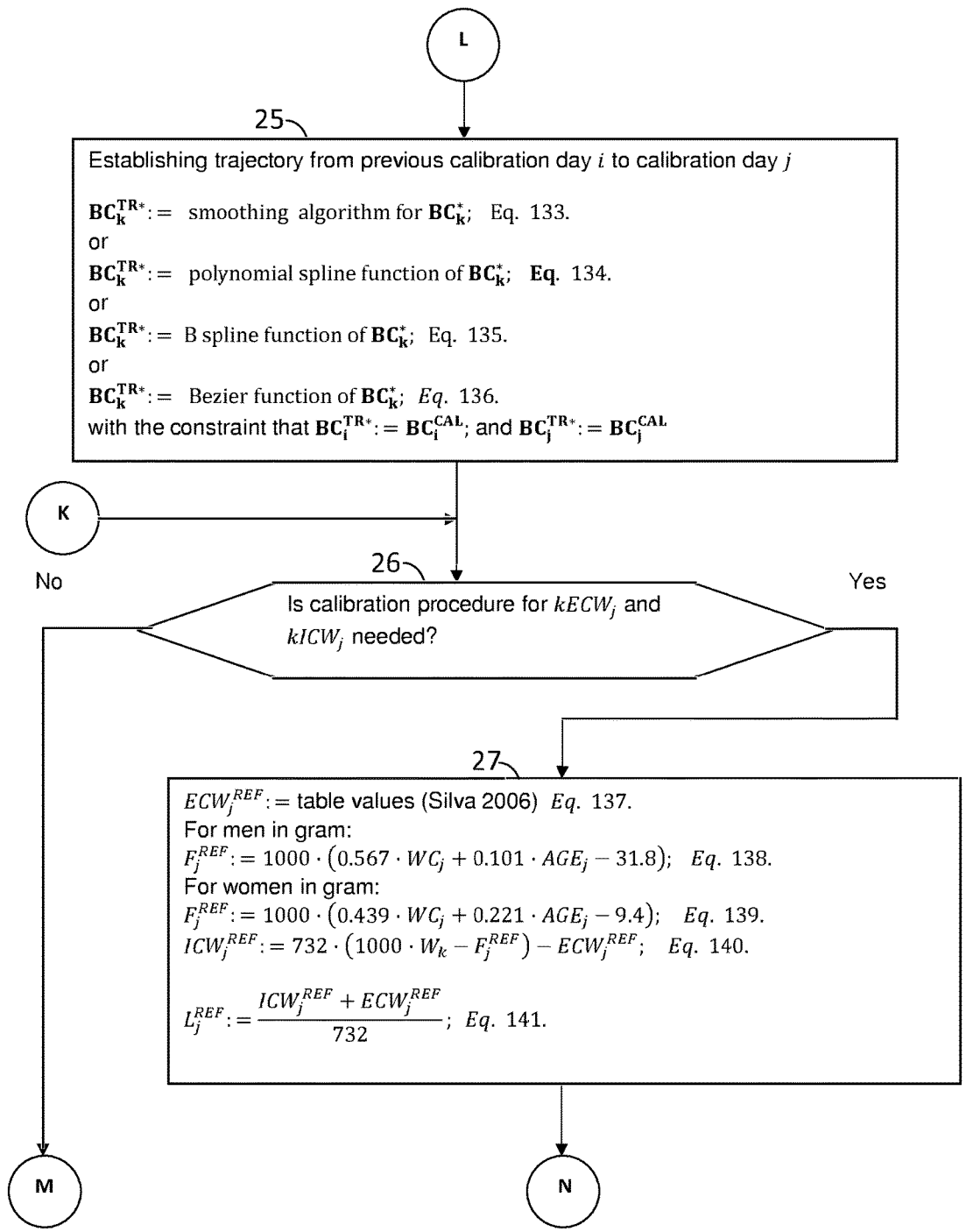
Figure 5K:
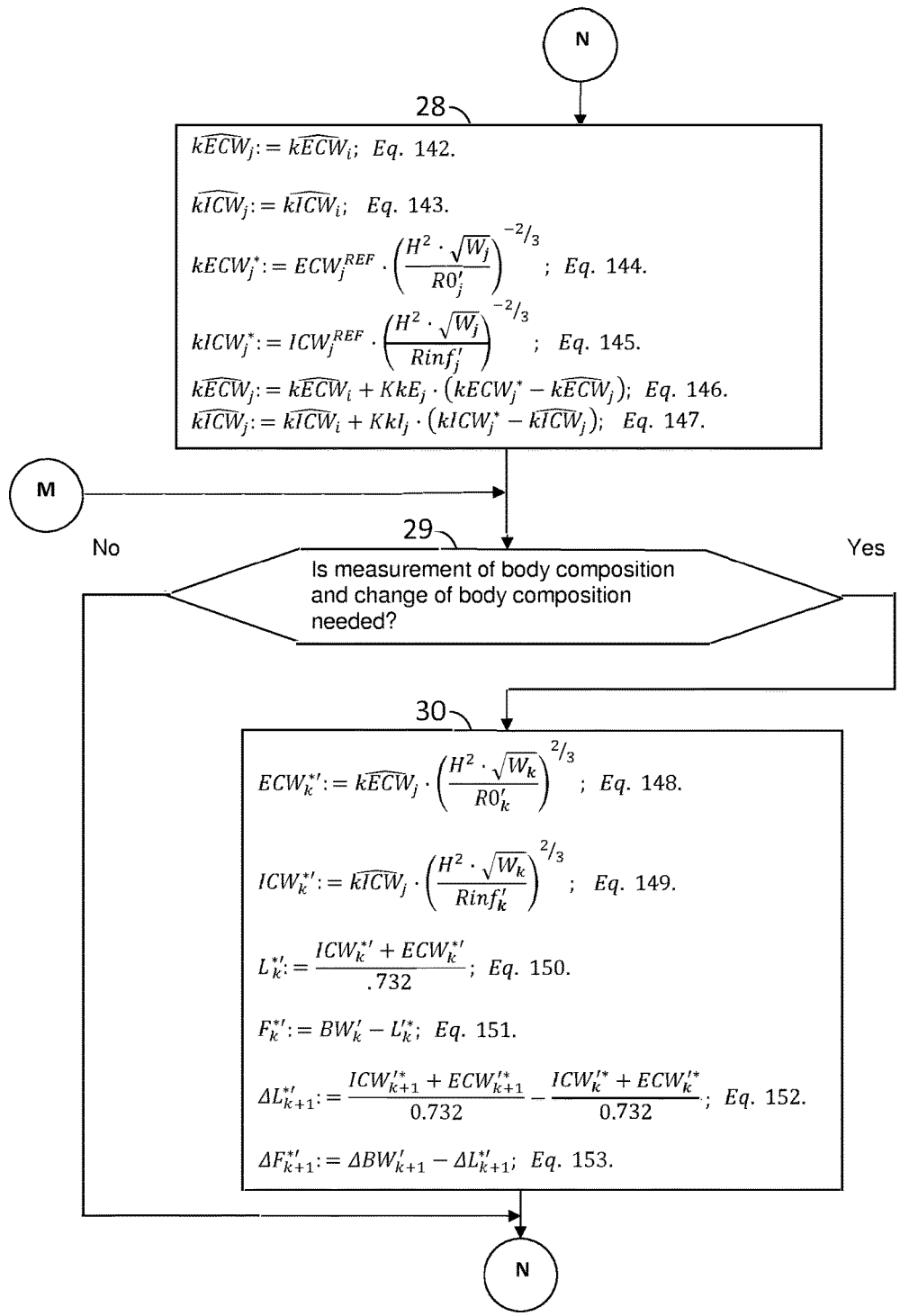
Figure 5L:
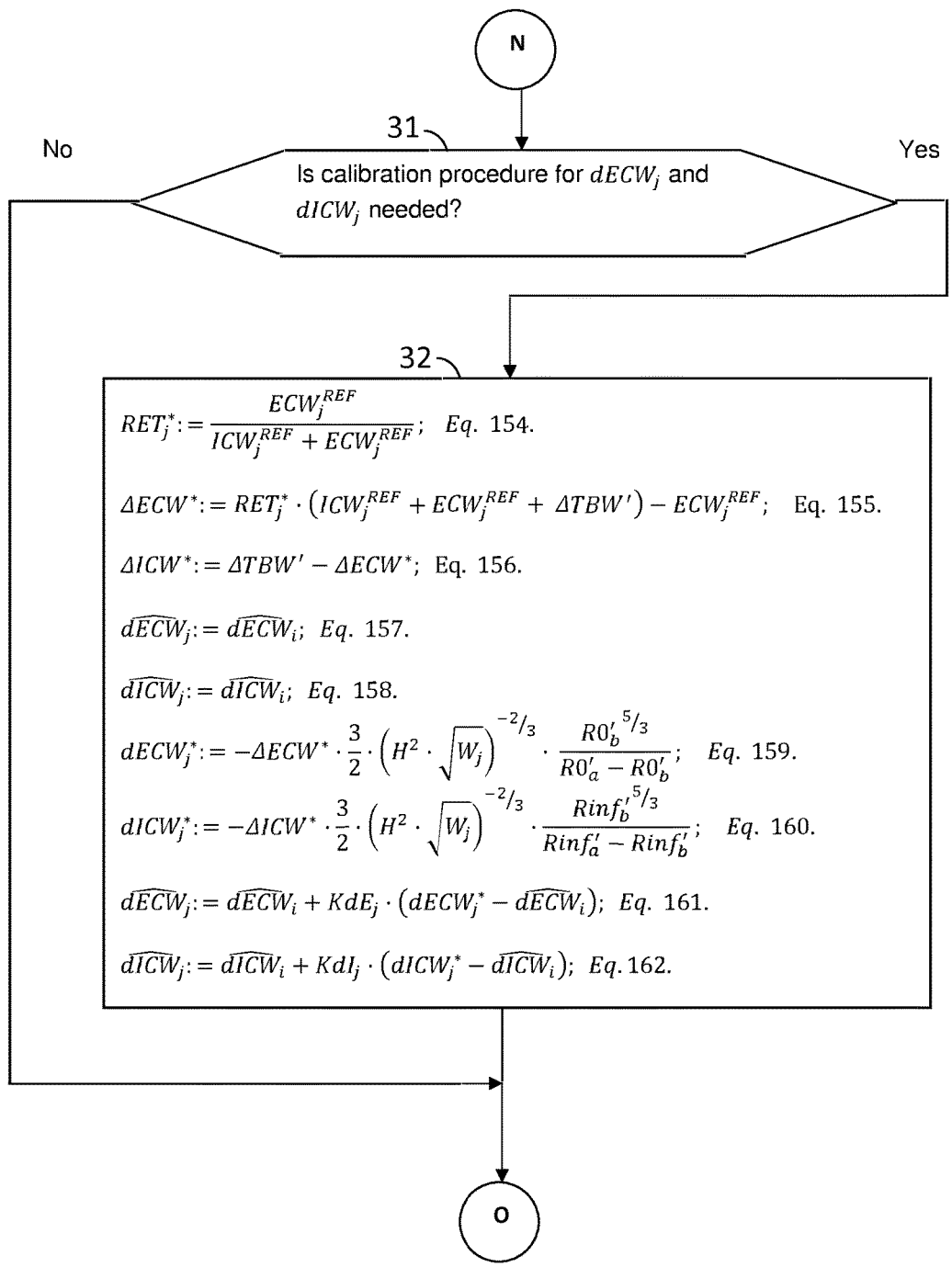
Figure 5M:
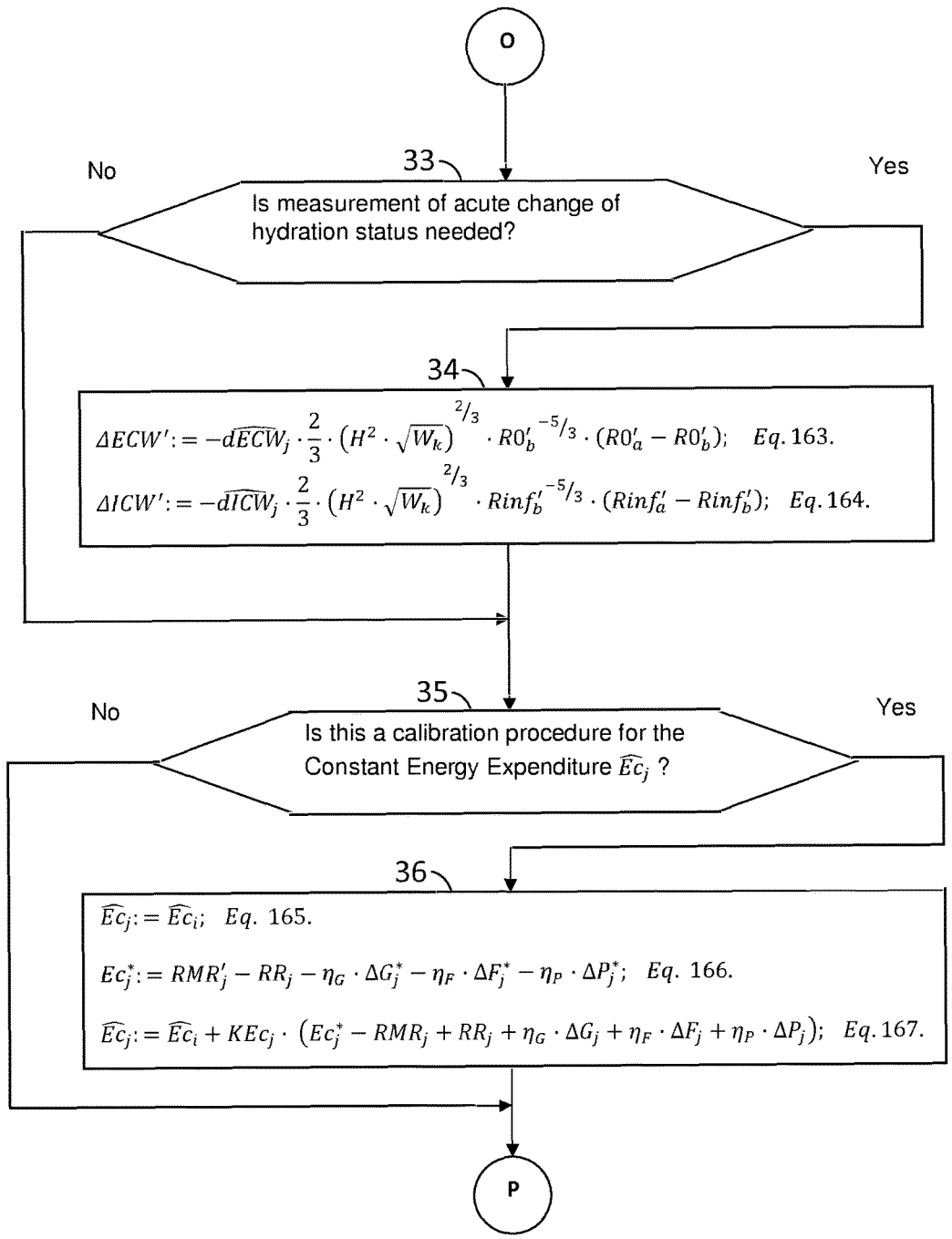
Figure 5N:
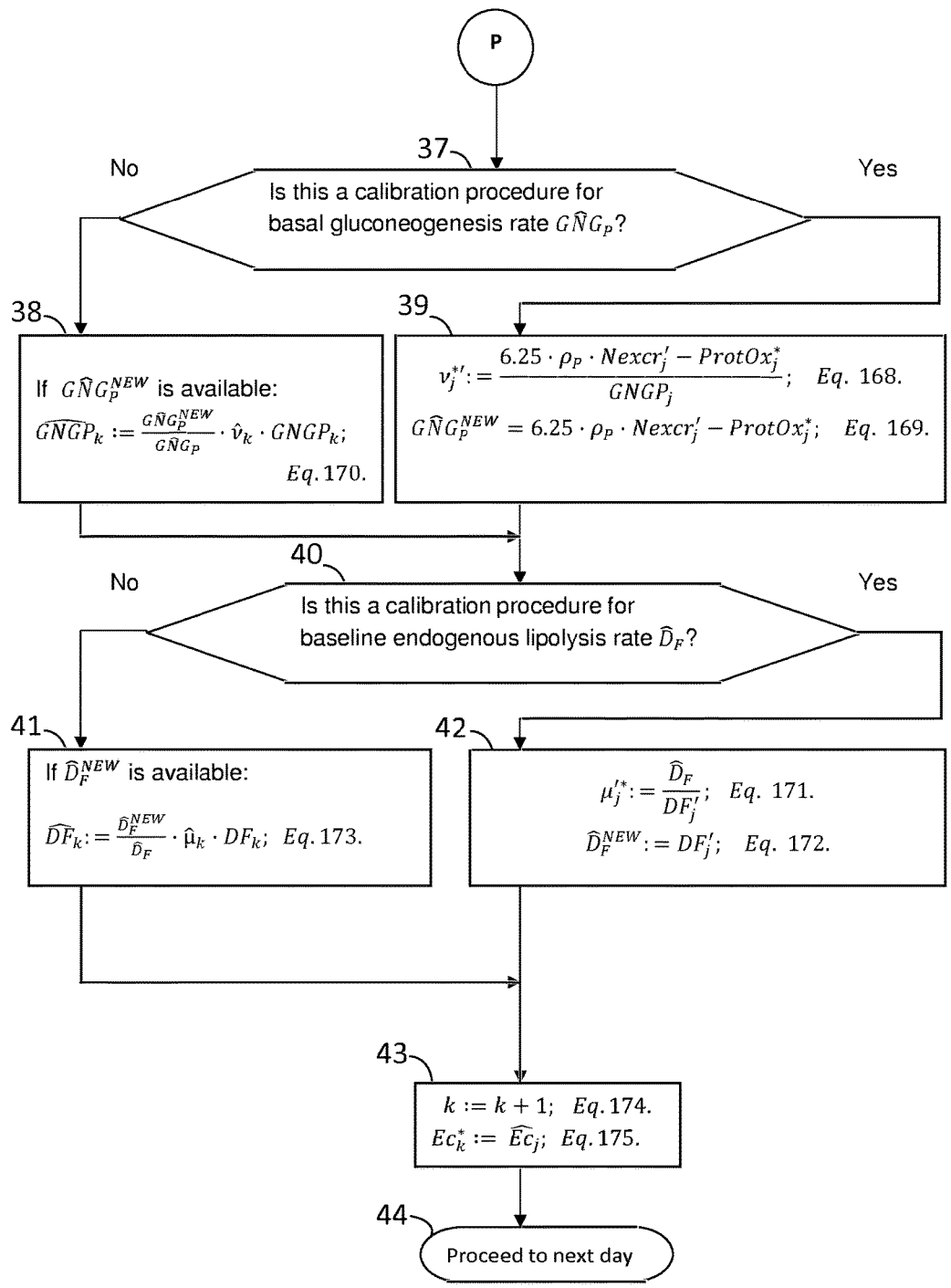

FIG. 5D $DP_{k-1} := \hat{D}_P \cdot \left(\frac{P_{k-1}}{P_0}\right);$ Eq. 52.

$DG_{k-1} := \hat{D}_G \cdot \left(\frac{G_{k-1}}{G_0}\right);$ Eq. 53.

$DFF_{k-1} := \frac{2}{3} \cdot \hat{D}_F \cdot \frac{F_{k-1}^{-1/3}}{F_0^{2/3}};$ Eq. 54.

$DFCI_0 := \hat{D}_F \cdot (-k_L/CI_0);$ Eq. 55.

$DF0_{k-1} := -DFF_{k-1} \cdot F_{k-1} - DFCI_0 \cdot CI_{k-2} + \hat{D}_F \cdot \left(k_L - k_L \cdot \frac{CI_{k-2}}{CI_0} + \left(\frac{F_{k-1}}{F_0}\right)^{2/3}\right);$ Eq. 56.

$DF_{k-1} := DFF_{k-1} \cdot F_{k-1} + DFCI_0 \cdot CI_{k-2} + DF0_{k-1};$ Eq. 57.
$DNLCI_0 := DFCI_0;$ Eq. 58.
$DNLG_{k-1} := \frac{DFF_{k-1} \cdot F_{k-1}}{G_{k-1}};$ Eq. 59.
$DNL0_{k-1} := DF0_{k-1};$ Eq. 60.
$DNL_{k-1} := DNLCI_0 \cdot CI_{k-2} + DNLG_{k-1} \cdot G_{k-1} + DNL0_{k-1};$ Eq. 61.
$GNGF_{k-1} := r_{GF} \cdot FI_{k-2} + r_G \cdot DF_{k-1};$ Eq. 62.
$GNGPP_0 := G\hat{N}G_P \cdot \frac{D_P}{P_0};$ Eq. 63.
$GNGPCI_0 := -G\hat{N}G_P \cdot \frac{\Gamma_C}{CI_0};$ Eq. 64.
$GNGPPI_0 := G\hat{N}G_P \cdot \frac{\Gamma_P}{PI_0};$ Eq. 65.
$GNGP0 := G\hat{N}G_P \cdot (\Gamma_C - \Gamma_P);$ Eq. 66.
$GNGP_{k-1} := GNGPP_0 \cdot P_{k-1} + GNGPCI_0 \cdot CI_{k-2} + GNGPPI_0 \cdot PI_{k-2} + GNGP0;$ Eq. 67.
$RR_{k-1} := \gamma_B \cdot M_B + \gamma_{BCM} \cdot (ICW_{k-1} + P_{k-1} + G_{k-1} + ICS - M_B) + \gamma_F \cdot F_{k-1}$
$\quad + (1 - \varepsilon_d) \cdot DNL_{k-1} + (1 - \varepsilon_g) \cdot (GNGP_{k-1} + GNGF_{k-1})$
$\quad + (\eta_P - \varepsilon_P) \cdot DP_{k-1} + \eta_F \cdot DF_{k-1} + \eta_G \cdot DG_{k-1};$ Eq. 68.
$SRMR_{k-1} := Ec_{k-1}^* + RR_{k-1} + \eta_G \cdot \Delta G_k^* + \eta_F \cdot \Delta F_k^* + \eta_P \cdot \Delta P_k^*;$ Eq. 69.
$r1_{k-1} := DNLCI_0 \cdot (1 - \varepsilon_d) + (r_G \cdot DFCI_0 + GNGPCI_0) \cdot (1 - \varepsilon_g) + \eta_F \cdot DFCI_0;$ Eq. 70.
$r2_{k-1} := r_{GF} \cdot (1 - \varepsilon_g);$ Eq. 71.
$r3_{k-1} := GNGPPI_0 \cdot (1 - \varepsilon_g);$ Eq. 72.

$DP_k := \widehat{D}_P \cdot \left(\dfrac{P_k}{P_0}\right);$ Eq. 73.

$DG_k := \widehat{D}_G \cdot \left(\dfrac{G_k}{G_0}\right);$ Eq. 74.

$DFF_k := \dfrac{2}{3} \cdot \widehat{D}_F \cdot \dfrac{F_k^{-1/3}}{F_0^{2/3}};$ Eq. 75.

$DFCI_0 := \widehat{D}_F \cdot (-k_L/CI_0);$ Eq. 76.

$DF0_k := -DFF_k \cdot F_k - DFCI_0 \cdot CI_{k-1} + \widehat{D}_F \cdot \left(k_L - k_L \cdot \dfrac{CI_{k-1}}{CI_0} + \left(\dfrac{F_k}{F_0}\right)^{2/3}\right);$ Eq. 77.

$DF_k := DFF_k \cdot F_k + DFCI_0 \cdot CI_{k-1} + DF0_k;$ Eq. 78.

$DNLCI_0 := DFCI_0;$ Eq. 79.

$DNLG_k := \dfrac{DFF_k \cdot F_k}{G_k};$ Eq. 80.

$DNL0_k := DF0_k;$ Eq. 81.

$DNL_k := DNLCI_0 \cdot CI_{k-1} + DNLG_k \cdot G_k + DNL0_k;$ Eq. 82.

$GNGF_k := r_{GF} \cdot FI_{k-1} + r_G \cdot DF_k;$ Eq. 83.

$GNGPP_0 := G\widehat{N}G_P \cdot \dfrac{\widehat{D}_P}{P_0};$ Eq. 84.

$GNGPCI_0 := -G\widehat{N}G_P \cdot \dfrac{\Gamma_C}{CI_0};$ Eq. 85.

$GNGPPI_0 := G\widehat{N}G_P \cdot \dfrac{\Gamma_P}{PI_0};$ Eq. 86.

$GNGP0 := G\widehat{N}G_P \cdot (\Gamma_C - \Gamma_P);$ Eq. 87.

$GNGP_k := GNGPP_0 \cdot P_k + GNGPCI_0 \cdot CI_{k-1} + GNGPPI_0 \cdot PI_{k-1} + GNGP0;$ Eq. 88.

$RR_k := \gamma_B \cdot M_B + \gamma_{BCM} \cdot (ICW_k + P_k + G_k - M_B) + \gamma_F \cdot F_k - (1 - \varepsilon_d) \cdot DNL_k$
$\qquad + (1 - \varepsilon_g) \cdot (GNGP_k + GNGF_k) + (\eta_P - \varepsilon_P) \cdot DP_k + \eta_F \cdot DF_k$
$\qquad + \eta_G \cdot DG_k;$ Eq. 89.

$SRMR_k := Ec_k^* + RR_k + \eta_G \cdot \Delta G_{k+1}^* + \eta_F \cdot \Delta F_{k+1}^* + \eta_P \cdot \Delta P_{k+1}^*;$ Eq. 90.

$r1_k := DNLCI_0 \cdot (1 - \varepsilon_d) + (r_G \cdot DFCI_0 + GNGPCI_0) \cdot (1 - \varepsilon_g) + \eta_F \cdot DFCI_0;$ Eq. 91.

$r2_k := r_{GF} \cdot (1 - \varepsilon_g);$ Eq. 92.

$r3_k := GNGPPI_0 \cdot (1 - \varepsilon_g);$ Eq. 93.

FIG. 5E

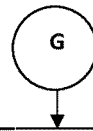

14

$$MMB_{k-1} := \begin{pmatrix} 1 & 1 & 1 \\ r1_{k-1} & r2_{k-1} & r3_{k-1} \\ 0 & 0 & 1 \end{pmatrix}; \quad Eq.\ 94.$$

$$MMA^*_{k-1} := \begin{pmatrix} -TEE^*_{k-1} \\ SRMR_{k-1} - Ec^*_{k-1} - RR_{k-1} \\ -6.25 \cdot \rho_P \cdot Nexcr_{k-1} \end{pmatrix}; \quad Eq.\ 95.$$

$$MMB_k := \begin{pmatrix} 1 & 1 & 1 \\ r1_k & r2_k & r3_k \\ 0 & 0 & 1 \end{pmatrix}; \quad Eq.\ 96.$$

$$MMA^*_k := \begin{pmatrix} -TEE^*_k \\ SRMR_k - Ec^*_k - RR_k \\ -6.25 \cdot \rho_P \cdot Nexcr_k \end{pmatrix}; \quad Eq.\ 97.$$

$UEI_{k-1} := MMB_k^{-1} \cdot MMB_{k-1};$  $Eq.\ 98.$ $UBC_{k-1} := MMB_k^{-1} \cdot Mc;$  $Eq.\ 99.$ $UC_{k-1} := MMB_k^{-1} \cdot (MMA^*_{k-1} - MMA^*_k - Mc \cdot \Delta BC^*_k);$  $Eq.\ 100.$ Linear Model of the Utilized Energy Intake (LM-UEI):
$EI_k := UEI_{k-1} \cdot EI_{k-1} + UBC_{k-1} \cdot \Delta BC^*_{k+1} + UC_{k-1};$  $Eq.\ 101.$ Measurement Model of the Utilized Energy Intake (M-UEI):
$EI_k^{RRE*} := MMB_k^{-1} \cdot Mc \cdot \Delta BC^*_{k+1} - MMB_k^{-1} \cdot MMA^*_k;$  $Eq.\ 102.$

15

STOCHASTIC IDENTIFICATION WITH INNOVATIONS REPRESENTATION
Self Correcting Model of the Utilized Energy Intake (S-EI):

If M-UEI is used:
$\delta \widehat{EI}^*_k := MMB_k^{-1} \cdot Mc \cdot \Delta BC^*_{k+1} - MMB_k^{-1} \cdot MMA^*_k - \widehat{EI}^*_{k-1};$  $Eq.\ 103$ If trajectory is used:
$\delta \widehat{EI}^*_k := MMB_k^{-1} \cdot Mc \cdot \Delta BC^{TR*}_{k+1} - MMB_k^{-1} \cdot MMA^*_k - \widehat{EI}^*_{k-1};$  $Eq.\ 104.$ $\widehat{EI}^*_k := UEI_{k-1} \cdot \widehat{EI}^*_{k-1} + UBC_{k-1} \cdot \Delta BC^*_{k+1} + UC_{k-1} + KU_k \cdot \delta \widehat{EI}^*_k;$  $Eq.\ 105.$ $EI_k := \widehat{EI}^*_k;$  $Eq.\ 106.$

FIG. 5F

APPARATUS AND METHOD FOR THE ANALYSIS OF THE CHANGE OF BODY COMPOSITION AND HYDRATION STATUS AND FOR DYNAMIC INDIRECT INDIVIDUALIZED MEASUREMENT OF COMPONENTS OF THE HUMAN ENERGY METABOLISM

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF INVENTION

Field

My apparatus and methods for the analysis of the change of body composition and hydration status and individualized mathematical modeling of the human energy metabolism relates generally to the measurement of the resistance and reactance of the human subject, to fitting mathematical models to serial measurements of indirectly measured lean body mass and fat mass, and to performing minimum variance estimation and prediction of variables of the human energy metabolism.

Prior Art

Biomedical engineering tools and multiple patented inventions of bioimpedance spectroscopy have been concerned with the problems of measuring the resistance and reactance of the human body at a multitude of frequencies in order to determine body composition and hydration status. Advancements in mathematical modeling of the human energy metabolism have provided tools to describe the relationship between energy balance, which is the difference of the energy intake and the total energy expenditure, and body composition changes. State space modeling coupled with the use of time variant minimum variance Kalman filtering or prediction has been successfully used in control engineering for over 50 years to observe and control state variables of complex dynamic systems. This technology holds great potential in monitoring difficult to measure daily body composition changes along with other essential components of the human energy metabolism in order to maximize capabilities of controlling them.

1. Background and Problem Identification with Bioimpedance Spectroscopy.

Bioimpedance spectroscopy has become a widely used technique in body composition and hydration status analysis in recent decades. The measurement of impedance, which is measuring resistance and reactance at frequencies from 1 to 1000 kHz, is purported to assist in the determination of extracellular and intracellular water mass. According to the Cole model of body impedance as interpreted by Cornish (Cornish, DOI: 10.1088/0031-9155/38/3/001), a current at low frequency flows through the extracellular water mass while at higher frequencies it flows through both the extracellular and intracellular water mass, allowing for extracellular and total water mass measurements. The Cole model fitted to resistances and reactances of the human subject at various frequencies can be extrapolated to the resistance values at zero and infinite frequencies. Using the resistance values at zero and infinite frequency, Moissl developed equations corrected with body mass index to calculate extracellular and intracellular water mass (Moissl, DOI: 10.1088/0967-3334/27/9/012). The problem with Moissl's equations was that they contained errors in the references, which accounted for the errors in the body mass index corrected extracellular and intracellular water mass calculation's accuracy (Moissl, DOI: 10.1088/0967-3334/27/9/012).

The errors in bioimpedance measurements of extracellular and intracellular water have hampered their accuracy and reliability. When using bioimpedance instruments, artefactual errors occur everywhere along the path of the flowing current around the entire electric circuit, which consists of current sources, a human subject, measurement electrodes, cable connections from subject to measuring instrument, and calibration elements. A disadvantage of the prior art, for example U.S. Pat. No. 5,280,429 (1994), is that the errors due to offset voltage and voltage noise at nodal junction points of the circuit elements cannot be determined, analyzed, and mitigated.

Moreover, at higher frequencies in bioimpedance spectroscopy, unexpected phase shifts in the results occur due to human subject stray capacitance and the instrument introduces distortions in the results due to nonlinearity. Errors due to stray capacitance are unavoidable in practice, uncontrollable to a large degree, and likely to be more pronounced where other devices are also attached to the subject, but they are measurable. A disadvantage of the prior art, for example U.S. Pat. No. 5,280,429 (1994), is that the errors due to stray capacitances and other measuring errors are neither determined, nor analyzed, nor reduced.

Another problem with the current bioimpedance spectroscopy technology is the variation in measurement results among machines due to the systemic errors introduced by the techniques, the instrumentation used, and other errors. The disadvantage of the prior art, for example U.S. Pat. No. 5,280,429 (1994), is that no effort was made to measure quality and inform the user about the size of the detectable error during measurement and about the reliability of the measurement results.

Another problem with bioimpedance measurements could be the placement of the preamplifier and the drivers of the shielded cables far away from the sensing electrodes. The disadvantage of such arrangements is that the magnitude of the interference from outside electromagnetic sources and the capacitive load from the shielded cables could cause suboptimal results. The prior art, for example U.S. Pat. No. 5,280,429 (1994), uses Fast Fourier Transformation, substituting summation for integration and evaluating only two wavelengths. These simplifications would be allowed if the analog to digital conversation were accurate, which it is not.

Advantages—Apparatus and Method for the Analysis of Change of Body Composition and Hydration Status Accordingly, several advantages of one or more aspects over the prior art in the field of bioimpedance spectroscopy are as follows:

a. Measuring and correcting for stray capacitance:

I measure all capacitances including stray capacitances. I measure the voltage at 6 measuring points along the current path. I apply Kirchhoff's first and second rule and Ohm's rule. All measurements have amplitude, offset, and phase value and I compare them to the zero phase value measured at reference resistances. The advantage of measuring voltage at nodal junctions and applying Kirchhoff's rules and Ohm's rule is that I am able to calculate the stray capacitance and measure its influence on the results.

b. Positioning the preamplifiers and the shield drivers close to the sensing electrodes:

The advantage of positioning the preamplifiers and the shield drivers close to the sensing electrodes is that the input noise will be kept low and no additional noise or capacitive load will be added.

c. Analyzing and removing errors and noise in the measuring circuit by using an input logic circuit:

I use switches to isolate or short circuit or leave intact parts of the measuring circuit without or with excitation at various frequencies. This allows for determining errors due to offset voltage and voltage noise due to various sources. The offset voltage is eliminated by subtracting the measured values at nodal junctions from the measured signal via a software algorithm. Hardware and/or software filtering remove voltage noise. The advantage of using an input logic circuit is that the apparatus will sense the offset voltage and voltage noise in the environment of operation and this allows for reduction of offset voltage and voltage noise.

d. A current source designed for high output resistance and low output reactance:

I use two mirrored Howland current sources which are fine tuned for their passive components to achieve high output resistance and low output reactance (Bertemes-Filho, DOI:10.4236/cs.2013.47059). This mirrored arrangement has the advantage that the output reactance is cut in half. I use two reference resistances for each current source. Using two reference resistances for each current source has the advantage that the current generated or sunk into the circuit will be known for each current source, allowing for precise network analysis. Using two mirrored Howland current sources has the advantage also that it creates a virtual floating earth potential, avoiding electric charge build up on the sensing electrodes.

e. Use of a sine wave fitting algorithm:

Sine wave fitting has the advantage of providing a priori knowledge of the exact value of the applied frequency of excitation, reducing the number of unknown variables. In statistical terms, sine fitting provides the minimum variance linear estimation for amplitude, phase, and offset. Sine fitting compensates better for the errors of the analog digital conversion than the Fast Fourier Transformation, which remains sensitive to such errors (Bertocco, DOI:10.1109/19.571881). Using a sine wave fitting algorithm over 6 to 16 wavelengths minimizes sampling error of the analog to digital converter. The sine fitting algorithm also gives a residual value, which I use to measure quality. The advantage of the use of the sine fitting algorithm is better overall noise reduction, allowing for elimination of offset voltage, minimization of voltage noise, and the ability to measure quality.

f. Non-linear curve fitting algorithm:

A Cole model with unknown resistance at zero and infinite frequency and unknown membrane capacitance is fitted to the resistance and reactance values at each examined frequency. The residual value, calculated as the difference between the measured and the model predicted value, is used to measure the quality of each individual measurement at each frequency. The sum of squared residual values measures the overall performance of the first embodiment of my apparatus. The advantage of measuring performance using the sum of squared residual values is that the user obtains quantified information of performance and of reliability of the function of the apparatus.

g. Creating individualized references for the measurement of body composition and hydration status change:

I overcome the problem that the equations corrected with body mass index contain errors in the references by establishing individual references for extracellular and intracellular water mass. The advantage of creating individualized references is that all of my measurements are individualized, referenced to individual reference values.

2. Background and Problem Identification with the Prior Art for Measuring Variables of the Human Energy Metabolism.

Decades of research into the causes of the obesity epidemic and related scientific research for the cause of it led to the creation of mathematical models of obesity. These models were based on the first law of thermodynamics and proffered that imbalance between energy intake and energy expenditure lead to changes in energy storage, primarily in lipids. The effort to quantify changes of the lipid store led Hall to construct mathematical models describing body composition changes matched to group averages (Hall, DOI: 10.1152/ajpendo.00523; DOI: 10.1109/MEMB.2009.935465; DOI: 10.1152/ajpendo.00559.2009). However, everyone's metabolism has unique characteristics, and individualized modeling is needed. Further, there is a need for real time metabolic modeling and tracking. The Hall models (Hall, DOI: 10.1152/ajpendo.00523; DOI: 10.1152/ajpendo.00559.2009) work off line when all data are available for retrospective analysis. Differential equations with infinitesimal time resolution are used in the Hall models, requiring significant software capacity to solve and knowledge of how the system changes during the 24 hour time period, when neither is needed for real time use and for measuring changes every 24 hour period. Importantly, the Hall model equations do not succeed in satisfying the constraint of conservation of energy i.e. the First Law of Thermodynamics, at the end of each day, which is essential for individualized real time modeling. Further, Hall does not consider the constraint that the model calculated body composition with its daily change together with changes of hydration status have to add up to the measured body weight and its daily change to allow for individualized real time modeling.

A long-felt but unsolved need for accurate and simplified tracking of body composition change, energy expenditure, and especially energy intake exists. The imprecision of current methods for determining these variables have precluded accurate quantification of the energy balance and thus precluded definitive statements regarding the cause of the obesity epidemic. The currently accepted method for tracking calorie intake in scientific studies of energy balance is self-reported calorie intake counting. For example, the daily ingested calories broken down into the three macronutrient groups are needed every day for the calculations in the Hall models. However, self-reported calorie intake counting is fraught with systemic errors (Hebert, DOI: 10.1016/S1047-2797(01)00297-6).

Model calculations of the macronutrient oxidation rate are an essential component of the modeling of the human energy metabolism. Hall (Hall, DOI: 10.1152/ajpendo.00523; DOI: 10.1152/ajpendo.00559.2009) created models for the macronutrient oxidation rates. However, Hall's equations are ad-hoc and are inherently nonlinear and not suitable for inverse calculations when model input is sought from known model output.

I have also found that problems of prediction and noise filtering exist in the dynamic modeling of the metabolism. The estimation or prediction of the state variables of a dynamic system model poses the challenges of ensuring accuracy and stability of estimations.

Advantages—Dynamic Indirect Individualized Measurement of Components of the Human Energy Metabolism Accordingly, several advantages of one or more aspects are as follows:
- a. Individualized self correcting and self adaptive modeling:

Individualized self correcting and self adaptive modeling is achieved through serial measurements of body composition changes and adjustment of the model parameters in a way that the model calculations approach the indirectly measured body composition changes or a target trajectory. Individualized self correcting and self adaptive modeling has the advantage that it reflects the state of the individual energy metabolism better than previous models, which were adjusted to grouped or averaged data points of a population.
- b. Real time calculations with recursive formulas and daily updates:

My models use recursive formulas which are updated daily with new data, eliminating the need to know all previous data points except for the last day's data during update and allowing for real time calculations of changes of body composition as they occur. The recursive method preserves the information gained from the last day's data without the need to store the information in the memory for calculations. The advantage of an algorithm using a recursive structure is that it is easy to use on portable computer devices and allows for making indirect measurements in freely moving human subjects.
- c. Applying linear invertible models:

The nonlinear equations used in the Hall model are very difficult or sometimes impossible to invert in order to calculate an unidentified input, the utilized energy intake, from a known output, the body composition change and energy expenditure. Also, the thermic effect of feeding is calculated implicitly in the Hall models, making inverse calculations to determine utilized energy intake rather difficult. I have also found that adaptive thermogenesis, as modeled by Hall with an ad-hoc formula, requires unnecessary assumptions and model parameter determinations when indirect measurement of the body composition can provide this information.

My model equations are linear and structured to support inverse calculations for unknown input variables, allowing for calculating the unknown macronutrient energy intake. The advantage of a linear invertible model is that by measuring the body composition change and using an inverse calculation, I determine the difficult to measure utilized macronutrient intake which was necessary to produce the measured body composition change in a freely moving human subject.
- d. Using difference equations:

Rather than using differential equations, which require continuous measurements and elaborate integration methods to solve, I use difference equations with 24 hour time resolution requiring model calculations only every 24 hours. The calculations require only matrix operations, eliminating the need for the knowledge of the exact course of changes during the 24 hour period. The advantage of using difference equations is that the explicit knowledge of how the metabolism arrived at the measured new state of body composition after a 24 hour time span is not required.
- e. State space method:

The state space method allows for interfacing error containing measurements through the use of a measurement model to a process model describing the metabolic process. The state-space method provides a convenient framework for the implementation of the time variant minimum variance Kalman estimation or prediction method.
- f. Calculating macronutrient oxidation rates:

I have found that macronutrient oxidation of carbohydrate, fat, and protein can be modeled for inverse calculation purposes using the principles of indirect calorimetry (Ferrannini, DOI: 10.1016/0026-0495(88)90110-2; Simonson, D. C. and R. A. DeFronzo. Indirect calorimetry: methodological and interpretative problems. American Journal of Physiology-Endocrinology and Metabolism. March 1990; 258(3):E399-E412.). I use the formulas introduced by Livesey, G. and Elia, M. (Livesey, G. and M. Elia. Estimation of energy expenditure, net carbohydrate utilization, and net fat oxidation and synthesis by indirect calorimetry: evaluation of errors with special reference to the detailed composition of fuels. American Journal of Clinical Nutrition. April 1988; 47(4):608-628.) to calculate macronutrient oxidation. The advantage of using these formulas is that they can be directly applied to my self adaptive individualized metabolic model of the human energy metabolism because they are linear and suitable for inverse calculations when model input is sought from known model output.
- g. Calculating daily utilized macronutrient intake values from ingested macronutrient calorie intake:

The input to my equations is the daily utilized macronutrient energy intake without thermic effect of feeding and the energy losses due to incomplete absorption. I calculate the thermic effect of feeding and the energy losses due to incomplete absorption from tabled values (Food and Nutrition Board, Institute of Medicine. Dietary Reference Intakes for Energy, Carbohydrate, Fiber, Fat, Fatty Acids, Cholesterol, Protein, and Amino Acids (Macronutrients): A Report of the Panel on Macronutrients, Subcommittees on Upper Reference Levels of Nutrients and Interpretation and Uses of Dietary Reference Intakes, and the Standing Committee On the Scientific Evaluation of Dietary Reference Intakes. http://www.nap.edu/books/0309085373/html/). The thermic effect of feeding and the energy losses due to incomplete absorption are subtracted from the ingested calories to obtain the daily utilized carbohydrate, fat, and protein intake. Calculating the daily utilized macronutrient values has the advantage that inverse calculations of the utilized energy intake become independent from the individual thermic effect of feeding or food absorption variables.
- h. Using the law of conversation of energy:

My energy equations take into account all major known processes of the human energy metabolism and are built to satisfy the law of conservation of energy at the end of a 24 hour period. I accommodate the so far unknown energy forms in the energy balance equation by using a correction factor for unknown energy losses or gains. Including a correction factor for unknown energy losses or gains has the advantage that it balances my energy equations so that they satisfy the law of conservation of energy. The correction factor for unknown energy losses or gains also serves as a measure of performance of my model, since the major components of the energy equation are included in my model and the expectation is that the unknown energy forms remain small.
- i. Estimating the daily utilized macronutrient intake values from indirectly measured body composition changes:

I use the time variant Kalman prediction method with innovations representation (Ljung, L. and T. Söderström. Theory and Practice of Recursive Identification. 1983; MIT Press, Cambridge, Mass., pp. 125.) for prediction and estimation of the unknown utilized macronutrient intake. For estimating the error of estimation I prefer using a reference or nominal trajectory method (Jazwinski, A. W. Stochastic Processes and Filtering Theory. 1970; Academic Press, Inc. New York, pp. 376.). The reference or nominal trajectory method has the advantage of enhancing the accuracy and stability of estimations. The advantage of utilizing the Kalman prediction, innovations representation, and the reference or nominal trajectory method is that I am able to estimate the daily utilized macronutrient intake in a freely moving human subject and require only daily measurement of the physical energy expenditure and determination of the body composition change along with an infrequently used calibration procedure.

j. Estimating the daily changes of the body composition and stochastic identification of the unidentified energy losses or gains, correction factor of the de novo lipogenesis, and correction factor for gluconeogenesis:

I use the time variant Kalman filtering method with innovations representation for estimation of the daily body composition change. I calculate the unknown energy losses or gains, the correction factor for de novo lipogenesis, and the correction factor for gluconeogenesis from amino acids with a stochastic identification method (Walter, E. and L. Pronzato. Identification of Parametric Models from Experimental Data. 1997; Springer Verlag Berlin, Paris, New York. pp. 114.). I prefer using a reference or nominal trajectory method (Jazwinski, A. W. Stochastic Processes and Filtering Theory. 1970; Academic Press, Inc. New York, pp. 376.) for estimating the daily body composition changes. My method has the advantage of enhancing accuracy and stability of estimations of daily body composition changes and allowing for dynamic indirect individualized measurement of components of the human energy metabolism in a freely moving human subject requiring only daily measurement of the physical energy expenditure and the determination of the body composition change along with an infrequently used calibration procedure for body composition and hydration status change.

These and other advantages of one or more aspects will become apparent from a consideration of the ensuing description and accompanying drawings.

SUMMARY

In accordance with one embodiment of an apparatus and method for the analysis of change of body composition and hydration status and for dynamic indirect individualized measurement of components of the human energy metabolism, my apparatus measures resistance and reactance of the human body directly at multiple frequencies, and I extrapolate indirectly to zero frequency and infinite frequency using the Cole model. I use individual reference values to calibrate my apparatus and method for the analysis of the change of body composition and hydration status. I calculate the extracellular water mass from the resistance at zero frequency and calculate the intracellular water mass from the resistance at infinite frequency.

My method for dynamic indirect individualized measurement of components of the human energy metabolism is comprised of the Self Correcting Model of the Utilized Energy Intake, the mathematical equations for components of the metabolism, and the Self Adaptive Model of the Human Energy Metabolism.

The input variables of the Self Correcting Model of the Utilized Energy Intake include the indirectly measured daily change of body composition, the directly measured total energy expenditure, and the indirectly calculated time-varying constant energy expenditure. I use the Kalman filtering method, the innovations representation method, and the reference or nominal trajectory method. The output is the estimated daily utilized macronutrient energy intake.

The input variables to the mathematical equations of the components of the human energy metabolism include either the ingested daily macronutrient energy intake comprised of carbohydrate, fat, and protein intake or the estimated daily utilized macronutrient energy intake. I use invertible linear equations. The output is the daily macronutrient oxidation rate, the daily resting metabolic rate, the daily unknown forms of energy losses or gains, the daily rate of endogenous lipolysis, the daily nitrogen excretion, and the daily gluconeogenesis from protein.

The input variables of the Self Adaptive Model of the Human Energy Metabolism include either the ingested daily macronutrient energy intake or the estimated daily utilized macronutrient intake. I use the Kalman filtering method, the innovations representation method, and the reference or nominal trajectory method. The output is the estimated daily change of the glycogen store, the fat store, and protein store; the daily correction factor for de novo lipogenesis; the daily correction factor for gluconeogenesis from amino acids; and the daily correction factor for unidentified energy losses or gains.

My apparatus and methods work in unison to create a noninvasive indirect individualized measurement of components of the human energy metabolism in a freely moving human subject.

DRAWINGS—FIGURES

FIG. 1. illustrates how the measurements of a device for body composition and hydration status analysis flow into a method for dynamic indirect individualized measurement of components of the human energy metabolism.

Figure 2:
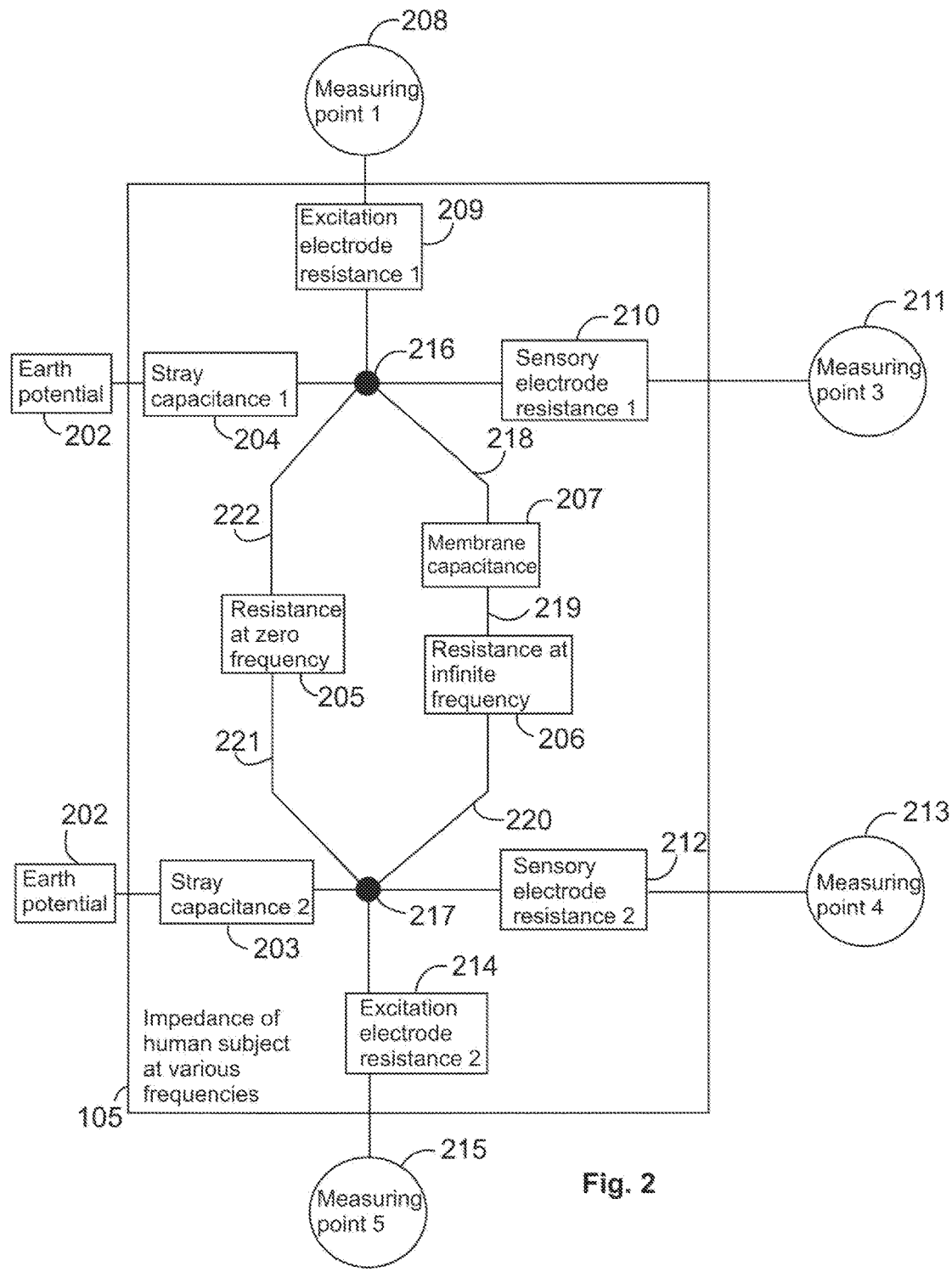

FIG. 2. illustrates an interface electrical connection between a human subject and measuring points.

Figure 3:
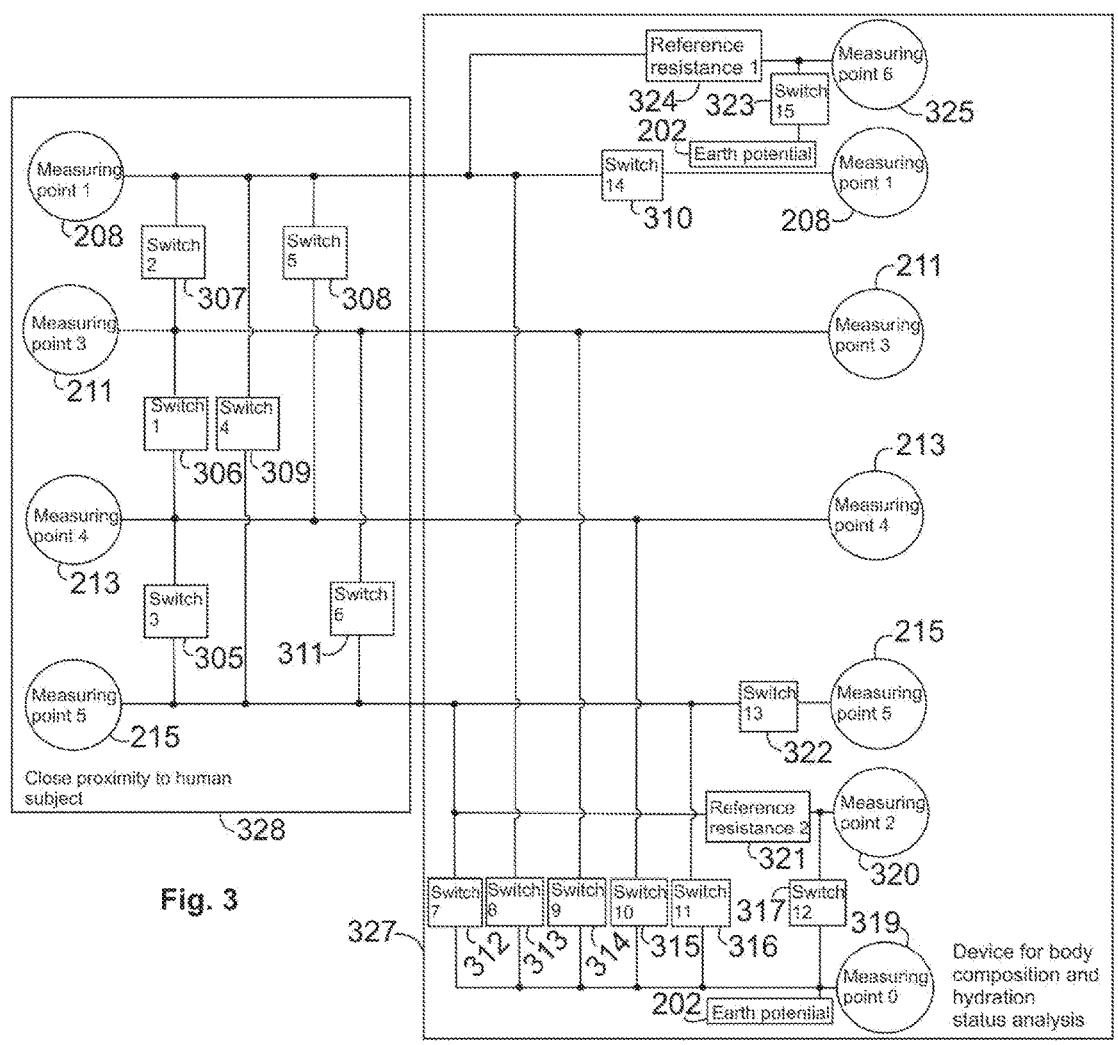

FIG. 3. illustrates an input logic circuit connecting measuring points.

Figure 4:
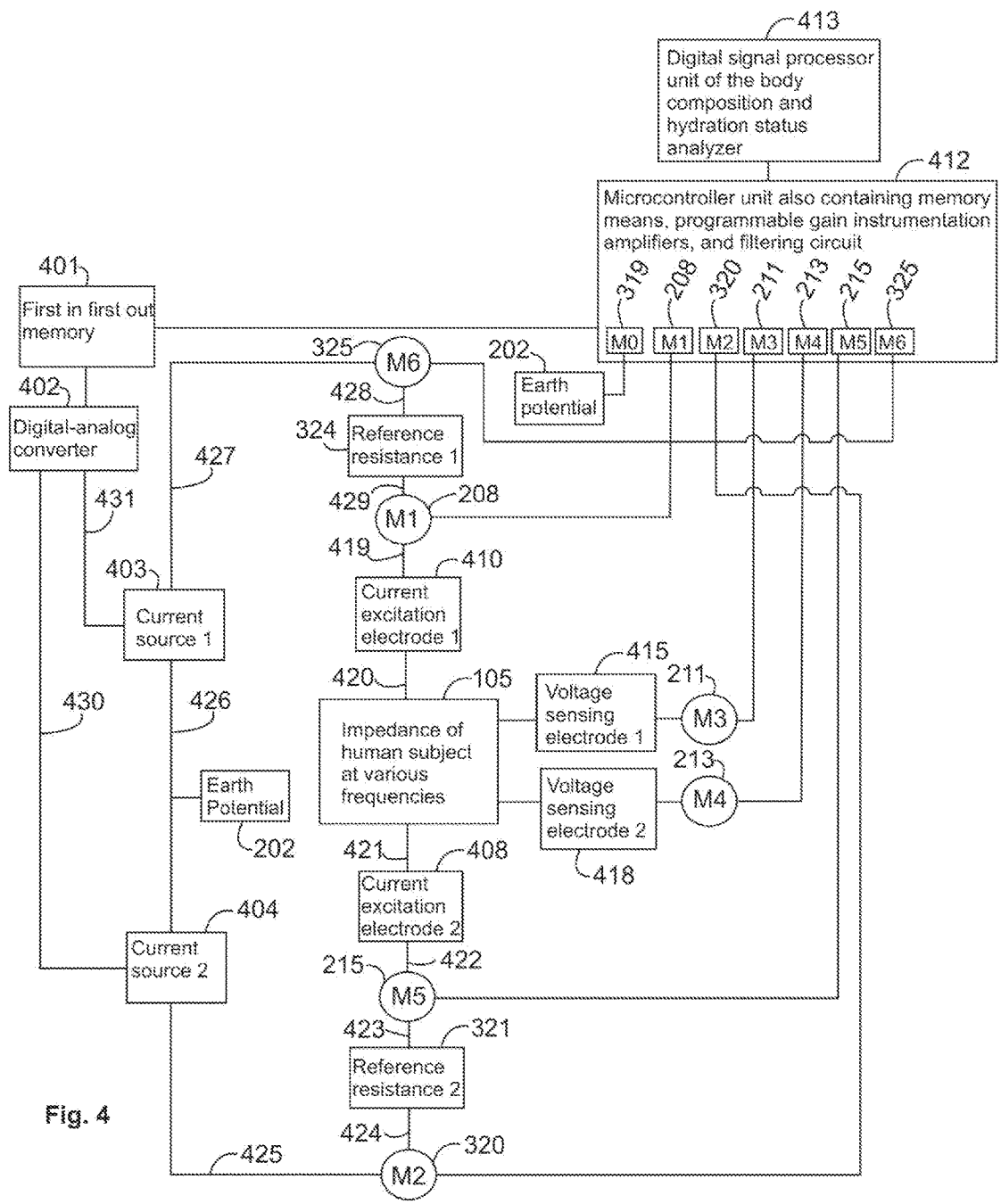

FIG. 4. illustrates the measuring circuit of the first embodiment to determine the impedance of a human subject at various frequencies.

FIG. 5. is a flow chart of the operation of the first method for the analysis of change of body composition and hydration status and for dynamic indirect individualized measurement of components of the human energy metabolism.

GLOSSARY

The following signs were used as an upper index:
~ ingested calorie
' measured quantity and the result comes from an outside source
\* indirectly calculated value
'\* indirectly calculated value using directly measured value
T transpose of a vector or matrix
CAL calibration value
TR\* indirectly calculated trajectory value
RRE\* calculated value obtained by using the Retained or Released Energy Model of the Human Energy Metabolism
REF reference value from outside source
The following signs were used as a lower index:
a value after a sentinel event of hydration status change
b value before a sentinel event of hydration status change
i value on calibration day i j value on calibration day j
k value on day k
k−1 value on day k−1
k−2 value on day k−2
k+1 value on day k+1
0 value on initiation day
The following sign was used for an estimated value:
  ˆ value is estimated with help of the Kalman filter or predictor
The following sign was used to assign a value to a variable:
  := algorithm step where the right side of the equation is evaluated first and assigned to the left side Scalar Variables
$AGE_k$ age (year)
$BCM_0$ body cell mass (g) at initiation day
$BCM_k$ body cell mass (g) at end of day k
$BW_0$ body weight (g) on initiation day
$BW_k$ body weight (g) on day k
$BW'_k$ measured body weight (g) on day k
BM bone mass (g)
$CarbOx_k$ rate of carbohydrate oxidation (kcal/day)
$CarbOx^*_k$ calculated rate of carbohydrate oxidation (kcal/day)
$CI_0$ utilized carbohydrate intake (kcal/day) at initiation day
$CI_k$ utilized carbohydrate intake in (kcal/day) on day k
$CI_{k-1}$ utilized carbohydrate intake in (kcal/day) on day k−1
$CI_{k-2}$ utilized carbohydrate intake in (kcal/day) on day k−2
$CIP_k^{REE*}$ utilized carbohydrate intake indirectly calculated by the Measurement Model of the Utilized Energy Intake from Body Composition Change on day k
$\widehat{CI}^*_k$ estimated indirectly calculated carbohydrate intake by the Self Correcting Model of the Utilized Energy Intake on day k
$\tilde{CI}_0$ ingested carbohydrate intake (kcal/day) at initiation day
$\tilde{CI}_k$ ingested carbohydrate intake (kcal/day) on day k
$\tilde{CI}_j$ ingested carbohydrate intake (kcal/day) on calibration day j
$dECW_j^{REF}$ reference value of the adjustable dynamic coefficient to calculate acute change of extracellular water mass on calibration day j
$dICW_j^{REF}$ reference value of the adjustable dynamic coefficient to calculate acute change of intracellular water mass on calibration day j
$\widehat{dECW}_j$ estimation of the adjustable dynamic coefficient to calculate acute change of extracellular water mass on calibration day j
$\widehat{dICW}_j$ estimation of the adjustable dynamic coefficient to calculate acute change of intracellular water mass on calibration day j
$DF_k$ rate of endogenous lipolysis (g/day) on day k
$DF'_j$ measured rate of endogenous lipolysis (g/day) on calibration day j
$\widehat{DF}_k$ estimated rate of endogenous lipolysis on day k with calibration
$DFF_0$ fat store dependent coefficient for rate of endogenous lipolysis at initiation day
$DFF_k$ fat store dependent coefficient for rate of endogenous lipolysis on day k
$DFF_{k-1}$ fat store dependent coefficient for rate of endogenous lipolysis on day k−1
$DFCI_0$ carbohydrate intake dependent coefficient for rate of endogenous lipolysis
$DF0_k$ bias for rate of endogenous lipolysis on day k
$DF0_{k-1}$ bias for rate of endogenous lipolysis on day k−1
$DG_k$ rate of glycogenolysis (g/day) on day k
$DG_{k-1}$ rate of glycogenolysis (g/day) on day k−1
$DNL_k$ rate of de novo lipogenesis (kcal/day) on day k
$DNL_{k-1}$ rate of de novo lipogenesis (kcal/day) on day k−1
$DNLG_k$ glycogen store dependent coefficient for rate of de novo lipogenesis on day k
$DNLG_{k-1}$ glycogen store dependent coefficient for rate of de novo lipogenesis on day k−1
$DNLCI_0$ carbohydrate intake dependent coefficient for rate of de novo lipogenesis
$DNLO_k$ bias for rate of endogenous lipolysis on day k
$DNLO_{k-1}$ bias for rate of endogenous lipolysis on day k−1
$DP_k$ rate of proteolysis (g/day) on day k
$DP_{k-1}$ rate of proteolysis (g/day) on day k−1
$Ec_k^*$ indirectly calculated time-varying constant energy expenditure (kcal) on day k
$Ec_{k-1}^*$ indirectly calculated time-varying constant energy expenditure (kcal) on day k−1
$\widehat{Ec}_i$ estimation of the indirectly calculated time-varying constant energy expenditure (kcal) on calibration day i
$\widehat{Ec}_j$ estimation of the indirectly calculated time-varying constant energy expenditure (kcal) on calibration day j
$Ec^*_j$ indirectly calculated time-varying constant energy expenditure (kcal) on calibration day j
ECP extracellular protein mass (g)
$ECW_0$ extracellular water mass (g) at initiation day
$ECW_k$ extracellular water mass (g) on day k
$ECW_{k-1}$ extracellular water mass (g) on day k−1
$ECW^{*'}_k$ indirectly measured extracellular water mass (g) on day k
$ECW_j^{REF}$ reference value for extracellular water mass (g) on calibration day j
$EFs_k$ energy needed for fat synthesis (kcal/day)
$EP_k$ energy production by substrate oxidation (kcal/day)
$F_0$ body fat mass (g) at initiation day
$F_k$ body fat mass (g) on day k
$F_{k+1}$ body fat mass (g) on day k+1
$F_{k-1}$ body fat mass (g) on day k−1
$FI_0$ utilized fat intake (kcal/day) at initiation day
$F^*_k$ indirectly calculated body fat mass (g) on day k
$F^*_{k+1}$ indirectly calculated body fat mass (g) on day k+1
$\hat{F}^*_{k+1}$ estimated indirectly calculated fat mass (g) on day k+1
$F^*_{k-1}$ indirectly calculated body fat mass (g) on day k−1
$F^{*'}_k$ indirectly measured body fat mass (g) on day k
$F_j^{REF}$ reference value for fat mass (g) on calibration day j
$FatOx_k$ rate of fat oxidation (kcal/day)
$FatOx^*_k$ calculated rate of fat oxidation (kcal/day)
$FI_k$ utilized fat intake (kcal/day) on day k
$FI_{k-1}$ utilized fat intake in (kcal/day) on day k−1
$FI_{k-2}$ utilized fat intake in (kcal/day) on day k−2
$FI_k^{RRE*}$ utilized fat intake indirectly calculated by Measurement Model of the Utilized energy Intake from Body Composition Change on day k
$\widehat{FI}^*_k$ estimated indirectly calculated fat intake by the Self Correcting Model of the utilized Energy Intake on day k
$\tilde{FI}_0$ ingested fat intake (kcal/day) at initiation day
$\tilde{FI}_k$ ingested fat intake (kcal/day) on day k
$\tilde{FI}_j$ ingested fat intake (kcal/day) on calibration day j
$G_0$ glycogen mass (g) at initiation day
$G_k$ glycogen mass (g) on day k
$G_{k+1}$ glycogen mass (g) on day k+1
$G_{k-1}$ glycogen mass (g) on day k−1
$G^*_k$ indirectly calculated glycogen mass (g) on day k
$G^*_{k+1}$ indirectly calculated glycogen mass (g) on day k+1
$\hat{G}^*_{k+1}$ estimated indirectly calculated glycogen mass (g) on day k+1

G*$_{k-1}$ indirectly calculated glycogen mass (g) on day k−1
G3P$_k$ glycerol 3-phosphate synthesis (kcal/day) on day k
GNGF$_k$ gluconeogenesis from glycerol in (kcal/day) on day k
GNGF$_{k-1}$ gluconeogenesis from glycerol in (kcal/day) on day k−1
GNGP0 bias for gluconeogenesis from protein
GNGP$_k$ gluconeogenesis from protein (kcal/day) on day k
$\widehat{GNGP}_k$ estimated gluconeogenesis from protein on day k with calibration
GNGP$_{k-1}$ gluconeogenesis from protein (kcal/day) on day k
GNGPP$_0$ protein store dependent coefficient for gluconeogenesis from protein
GNGPCI$_0$ carbohydrate intake dependent coefficient for gluconeogenesis from protein
GNGPPI$_0$ protein intake dependent coefficient for gluconeogenesis from protein
H body height (cm)
i index variable showing the day of the calibration before the last
ICW$_0$ intracellular water mass (g) at initiation day
ICW$_k$ intracellular water mass (g) on day k
ICW$_{k-1}$ intracellular water mass (g) on day k−1
ICW*'$_k$ indirectly measured intracellular water mass (g) on day k
ICW$_j^{REF}$ reference value for intracellular water mass (g) on calibration day j
j index variable showing day of the last calibration
k index variable for the day k
KdE$_k$ Kalman gain of the adjustable dynamic coefficient to calculate the daily change of the extracellular water mass for day k−1
KdI$_k$ Kalman gain of the adjustable dynamic coefficient to calculate the daily change of the intracellular water mass for day k−1
KEc$_j$ Kalman gain of the indirectly measured constant energy expenditure
kECW$_j^{REF}$ reference value of the adjustable coefficient to calculate to calculate extracellular water mass on day k
kICW$_j^{REF}$ reference value of the adjustable coefficient to calculate intracellular water mass on day k
$\widehat{kECW}_k$ estimation of the adjustable coefficient to calculate extracellular water mass on day k
$\widehat{kICW}_k$ estimation of the adjustable coefficient to calculate intracellular water mass on day k
KkE$_k$ Kalman gain of the adjustable coefficient to calculate extracellular water mass on day k
KkI$_k$ Kalman gain of the adjustable coefficient to calculate intracellular water mass on day k
Kμ$_k$ Kalman gain of the correction factor for de novo lipogenesis
Kv$_k$ Kalman gain of the correction factor for gluconeogenesis from amino acids
Kφ$_k$ Kalman gain of the correction factor for unknown energy losses or gains
L$_0$ lean body mass (g) on initiation day
L$_k$ lean body mass (g) on day k
$\tilde{L}_k$ indirectly measured lean body mass (g) on day k
Nexcr$_k$ nitrogen excretion on day k (g/day)
Nexcr'$_j$ measured nitrogen excretion (g/day) on calibration day j
P$_0$ protein mass (g) at initiation day
P$_k$ protein mass (g) on day k
P$_{k+1}$ protein mass (g) on day k+1
P*$_{k+1}$ estimated indirectly calculated protein mass (g) on day k+1
P$_{k-1}$ protein mass (g) on day k−1
P*$_k$ indirectly calculated body protein mass (g) on day k
P*$_{k+1}$ indirectly calculated body protein mass (g) on day k+1
P*$_{k-1}$ indirectly calculated body protein mass (g) on day k−1
ProtOx$_k$ rate of protein oxidation (kcal/day)
ProtOx*$_k$ calculated rate of protein oxidation (kcal/day)
PAE'$_k$ physical activity energy expenditure (kcal/day)
PI$_0$ utilized protein intake (kcal/day) at initiation day
PI$_k$ utilized protein intake (kcal/day) on day k
PI$_{k-1}$ utilized protein intake (kcal/day) on day k−1
PI$_{k-2}$ utilized protein intake (kcal/day) on day k−2
PI$_k^{RRE*}$ utilized protein intake indirectly calculated by the Measurement Model of the Utilized Energy Intake from Body Composition Change on day k
$\widehat{PI}^*_k$ estimated indirectly calculated protein intake by the Self Correcting Model of the Utilized Energy Intake on day k
PI$_0^\sim$ ingested protein intake (kcal/day) at initiation day
PI$_k^\sim$ ingested protein intake (kcal/day) on day k
PI$_j^\sim$ ingested protein intake (kcal/day) on calibration day j
r$_{FFA}$ molecular weight ratio free fatty acid to triglyceride
r$_{GF}$ molecular weight and energy density ratio glycerol to triglyceride
r$_{GF}$ molecular weight ratio glycerol to triglyceride
r1$_k$ part of the resting metabolic rate which is dependent on the utilized carbohydrate intake on day k
r2$_k$ part of the resting metabolic rate which is dependent on the utilized fat intake on day k
r3$_k$ part of the resting metabolic rate which is dependent on the utilized protein intake on day k
r1$_{k-1}$ part of the resting metabolic rate which is dependent on the utilized carbohydrate intake on day k−1
r2$_{k-1}$ part of the resting metabolic rate which is dependent on the utilized fat intake on day k−1
r3$_{k-1}$ part of the resting metabolic rate which is dependent on the utilized protein intake on day k−1
R0$_k$ resistance extrapolated at zero frequency
Rinf$_k$ resistance extrapolated at infinite frequency
R0'$_a$ resistance extrapolated at zero frequency after a sentinel event of hydration change
R0'$_b$ resistance extrapolated at zero frequency before a sentinel event of hydration change
Rinf'$_a$ resistance extrapolated at infinite frequency after a sentinel event of hydration change
Rinf'$_b$ resistance extrapolated at infinite frequency before a sentinel event of hydration change
RR$_k$ part of the resting metabolic rate which is independent of the body composition changes and the time-varying constant energy expenditure on day k
RR$_{k-1}$ part of the resting metabolic rate which is independent of the body composition changes and the time-varying constant energy expenditure on day k−1
RET*$_j$ ratio of extracellular to total water mass ratio calculated on calibration day with index mark j
RRE$_k$ retained or released energy from body stores for day k
RMR$_k$ resting metabolic rate (kcal/day) with filtering formula on day k
RMR$_j$ resting metabolic rate (kcal/day) with predictive formula on calibration day j
RMR'$_j$ measured resting metabolic rate on calibration day j
SRMR$_k$ resting metabolic rate (kcal/day) with predictive formula on day k $SRMR_{k-1}$ resting metabolic rate (kcal/day) with predictive formula on day k−1

$TEE*_k$ indirectly calculated total energy expenditure (kcal/day) on day k $TBW_k$ total body water mass (g)

$W_k$ body weight (kg) on day k $WC_k$ waist circumference (cm)

$\hat{\mu}_0$ estimation of the correction factor for de novo lipogenesis at initiation day $\hat{\mu}_k$ estimation of the correction factor for de novo lipogenesis on day k $\mu*_k$ indirectly calculated correction factor for de novo lipogenesis $\mu*_j$ indirectly measured correction factor for de novo lipogenesis on calibration day j $\hat{v}_0$ estimation of the correction factor for gluconeogenesis from amino acids at initiation day $\hat{v}_k$ estimation of the correction factor for gluconeogenesis from amino acids on day k $\hat{v}*_k$ indirectly calculated correction factor for gluconeogenesis from amino acids $\hat{v}'_j*$ indirectly measured correction factor for gluconeogenesis from amino acids on calibration day j $\hat{\varphi}_0$ estimation of the correction factor for unknown energy losses or gains at initiation day $\hat{\varphi}_k$ estimation of the unknown energy losses or gains on day k $\hat{\varphi}*_k$ indirectly calculated correction factor for unidentified energy losses or gains Vector Variables $BC_k$ body composition vector with elements of size of glycogen, fat, and protein stores on day k $BC*_k$ indirectly calculated body composition vector on day k $BC_i^{CAL}$ body composition vector with elements of size of glycogen, fat, and protein stores obtained through calibration procedure on day i $BC_j^{CAL}$ body composition vector with elements of size of glycogen, fat, and protein stores obtained through calibration procedure on day j $BC_i^{SM*}$ smoothed indirectly calculated body composition vector on day k $BC_k^{TR*}$ body composition vector with elements of size of glycogen, fat, and protein stores obtained through trajectory calculation procedure on day i $BC_k^{TR*}$ body composition vector with elements of size of glycogen, fat, and protein stores obtained through trajectory calculation procedure on day k $C_k$ bias vector in the Linear Extended Model of the Human Energy Metabolism on day k $EI_k$ utilized energy intake vector with elements of daily metabolized macronutrient intake carbohydrate, fat, and protein on day k $\delta EI_k^*$ deviation of the estimated indirectly calculated utilized energy intake from trajectory on day k $EI_k^{RRE*}$ indirectly measured utilized energy Intake on day k using the Retained or Released Energy Model of the Human Energy Metabolism $\widehat{EI}_k^*$ estimated indirectly calculated utilized energy intake by the Self Correcting Model of the Utilized Energy Intake on day k $\widehat{EI}_{k-1}^*$ estimated indirectly calculated utilized energy intake by the Self Correcting Model of the Utilized Energy Intake on day k−1

$HEE*_k$ indirectly calculated heat energy equivalent vector on day k $Ox_k$ macronutrient oxidation vector with elements of energy obtained from oxidation of carbohydrate, fat, and protein on day k $Ox*_k$ indirectly calculated macronutrient oxidation vector with elements of energy obtained after oxidation of carbohydrate, fat, and protein on day k $UC_k$ time varying bias vector in Self Corrective Model of the Utilized Energy Intake on day k $UC_{k-1}$ time varying bias vector in Self Corrective Model of the Utilized Energy Intake on day k−1

$\delta\widehat{BC}_{k+1}^*$ deviation of the estimated indirectly calculated change of body composition vector from trajectory of day k $\Delta BC_k$ change of body composition vector of day k−1

$\Delta BC_{k+1}$ change of body composition vector of day k $\Delta BC*_{k+1}$ indirectly calculated change of body composition vector of day k $\Delta BC_{k+1}*$ change of trajectory of indirectly calculated change of body composition vector of day k $\Delta\widehat{BC}_{k+1}^*$ estimated indirectly calculated change of body composition vector of day k $\Delta LFP*_{k+1}$ change of the indirectly calculated Lean-Fat-Protein vector for day k $\Delta LFR_{k+1}$ change of the indirectly calculated Lean-Fat-Resting-Metabolic-Rate vector for day k Matrix Variables $A_k$ dynamic transition matrix of the Linear Extended Model of the Human Energy Metabolism $B_k$ input coupling matrix of the Linear Extended Model of the Human Energy Metabolism He oxygen caloric heat equivalent constants matrix $He^{-1}$ inverse matrix of the oxygen caloric heat equivalent constants matrix $KH_k$ Kalman gain matrix of the Self Adaptive Model of the Human Energy Metabolism $KU_k$ Kalman gain matrix of the Self Correcting Model of the Utilized Energy Intake Mc energy constant matrix of the Retained or Released Energy Model of the Human Energy Metabolism $MMA*_k$ indirectly calculated bias vector of the Retained or Released Energy Model of the Human Energy Metabolism on day k $MMA*_{k-1}$ indirectly calculated bias vector of the Retained or Released Energy Model of the Human Energy Metabolism on day k−1

MNB constant matrix of the Measurement Model of Body Composition Change from Lean-Fat-Protein $MMB_k$ time varying utilized energy intake coupling matrix in the Retained or Released Energy Model of the Human Energy Metabolism on day k $MMB_{k-1}$ time varying utilized energy intake coupling matrix in the Retained or Released Energy Model of the Human Energy Metabolism on day k−1

$MMB_k^{-1}$ inverse matrix of the time varying utilized energy intake coupling matrix in the Retained or Released Energy Model of the Human Energy Metabolism on day k MRB constant matrix of the Measurement Model of Body Composition Change from Lean-Fat-Resting Metabolic Rate $UBC_{k-1}$ dynamic coupling matrix in the Self Corrective Model of the Utilized Energy Intake on day k−1
$UEI_{k-1}$ dynamic transition matrix in the Self Correcting Model of the Utilized Energy Intake on day k−1
Dynamic System or Process Models
LEM-HEM Linear Extended Model of the Human Energy Metabolism:

$$\rho_C \cdot \Delta G_{k+1} := CI_k + \hat{v}_k \cdot GNGP_k + GNGF_k - \hat{\mu}_k \cdot DNL_k - G3P_k - EFs_k - CarbOx^*_k - \hat{\varphi}_k;$$

$$\rho_F \cdot \Delta F_{k+1} := r_{FFA} \cdot FI_k + \hat{\mu}_k \cdot DNL_k + r_G \cdot \Delta F_{k+1} FatOx^*_k;$$

$$\rho_P \cdot \Delta P_{k+1} := PI_k - \hat{v}_k \cdot GNGP_k - ProtOx^*_k;$$

or the equivalent with matrix notation:

$$\Delta BC_{k+1} := A_k \cdot BC_k + B_k \cdot EI_k + C_k;$$

LM-HEM Linear Model of the Human Energy Metabolism:

$$\rho_C \cdot \Delta G_{k+1} := CI_k + GNGP_k + GNGF_k - DNL_k - G3P_k - EFs_k - CarbOx^*_k;$$

$$\rho F \cdot \Delta F_{k+1} := r_{FFA} \cdot FI_k + DNL_k + r_G \cdot \Delta F_{k+1} - FatOx_k;$$

$$\rho_P \cdot \Delta P_{k+1} := PI_k - GNGP_k - ProtOx^*_k;$$

RRE-HEM Retained or Released Energy Model of the Human Energy Metabolism $$\rho_C \cdot \Delta G^*_{k+1} + \rho_F \cdot \Delta F^*_{k+1} + \rho_P \cdot \Delta P^*_{k+1} = CI_k + FI_k + PI_k - TEE_k;$$

$$\eta_G \cdot \Delta G^*_{k+1} + \eta_F \cdot \Delta F^*_{k+1} + \eta_P \cdot \Delta P^*_{k+1} = SRMR_k - Ec^*_k - RR_k;$$

$$\rho_P \cdot \Delta P_{k+1} := PI_k - 6.25 \cdot \rho_P \cdot Nexcr_k;$$

or the equivalent with matrix notation:

$$Mc \cdot \Delta BC_{k+1} := MMB_k \cdot EI_k^{RRE*} + MMA^*_k;$$

F-RMR Filtering Model of the Resting Metabolic Rate $$RMR_k := Ec^*_k + RR_k + \eta_G \cdot \Delta G_k + \eta_F \cdot \Delta F_k + \eta_P \cdot \Delta P_k;$$

P-RMR Predicting Model of the Resting Metabolic Rate $$SRMR_k := Ec^*_k + RR_k + \eta_G \cdot \Delta G^*_{k+1} + \Delta_F \cdot \Delta F^*_{k+1} + \eta_P \cdot \Delta P^*_{k+1};$$

LM-UEI Linear Model of the Utilized Energy Intake $$EI_k := UEI_{k-1} \cdot EI_{k-1} + UBC_{k-1} \cdot \Delta BC^*_{k+1} + UC_{k-1};$$

S-EI Self Correcting Model of the Utilized Energy Intake $$\widehat{EI}^*_k := UEI_{k-1} \widehat{EI}^*_{k-1} + UBC_{k-1} \cdot \Delta BC_{k+1} + UC_{k-1} + KU_k \cdot \delta \widehat{BC}^*_{k+1};$$

SAM-HEM Self Adaptive Model of the Human Energy Metabolism $$\Delta \widehat{\Delta BC}^*_{k+1} := A_k \cdot \widehat{BC}^*_k + B_k \cdot EI_k + C_k + KH_k \cdot \delta \widehat{BC}^*_k;$$

Measurement Models
M-LFP Measurement Model of Body Composition Change from Lean-Fat-Protein $$\Delta LFP^*_{k+1} := MNB \cdot \Delta BC^*_{k+1};$$

M-LFR Measurement Model of Body Composition Change from Lean-Fat-Resting-Metabolic-Rate $$\Delta LFR^*_{k+1} := MRB \cdot \Delta BC^*_{k+1};$$

M-RRE Measurement Model of Body Composition Change from the Retained or Released Energy $$Mc \cdot \Delta BC^*_{k+1} := MMB_k \cdot EI_k + MMA^*_k;$$

M-UEI Measurement Model of the Utilized Energy Intake from Body Composition Change $$EI_k^{RRE*} := MMB_k^{-1} \cdot Mc \cdot \Delta BC^*_{k+1} \cdot MMB_k^{-1} \cdot MMA^*_k;$$

M-Ox Measurement Model of the Macronutrient Oxidation Rates $$Ox^*_k := He^{-1} \cdot HEE^*_k$$

Model Constants
The following model constants were taken from Hall (Hall, DOI: 10.1152/ajpendo.00523):
$\hat{D}_F$ 140 g·day$^{-1}$ baseline lipolysis rate before calibration
$\hat{D}_F^{NEW}$ new value for the baseline lipolysis rate after calibration on day j
$\hat{D}_P$ 300 g·day$^{-1}$ baseline proteolysis rate
$\hat{D}_G$ 180 g·day$^{-1}$ baseline glycogenolysis rate
$GNG_P$ 100 kcal·day$^{-1}$ basal gluconeogenesis rate before calibration
$GNG_P^{NEW}$ new value for the basal gluconeogenesis rate after calibration on day j
$k_L$ 3.0910 dimensionless normalized lipolysis rate
$M_B$ 1.4 kg brain mass
$M_G$ 92 g/mol molecular mass of glycerol
$M_{TG}$ 860 g/mol molecular mass of triglyceride
$M_{FFA}$ 273 g/mol molecular mass of free fatty acids
co 0.746 liters of oxygen is needed to burn 1 g glucose
fo 2.03 liters of oxygen is needed to burn 1 g fat
po 0.966 liters of oxygen is needed to burn 1 g protein
cc 0.746 liters of carbon dioxide is produced when 1 g of glucose is burned
fc 1.43 liters of carbon dioxide is produced when 1 g of fat is burned
pc 0.782 liters of carbon dioxide is produced when 1 g of protein is burned
$\alpha_C$ 0.075 dimensionless thermal effect of feeding factor for ingested carbohydrate
$\alpha_P$ 0.025 dimensionless thermal effect of feeding factor for ingested fat
$\alpha_P$ 0.25 dimensionless thermal effect of feeding factor for ingested protein
$\gamma_B$ 240 kcal·kg$^{-1}$·day$^{-1}$ metabolic rate for the brain
$\gamma_F$ 4.5 kcal·kg$^{-1}$·day$^{-1}$ metabolic rate for adipose tissue
$\gamma_{BCM}$ 24 kcal·kg$^{-1}$·day basal metabolic rate
$\varepsilon_P$ 0.17 kcal/g protein degradation cost
$\varepsilon_d$ 0.8 dimensionless de novo lipogenesis efficiency
$\varepsilon_g$ 0.8 dimensionless gluconeogenesis efficiency
$\eta_F$ 0.18 kcal/g synthesis cost of fat
$\eta_P$ 0.86 kcal/g synthesis cost of protein
$\eta_G$ 0.21 kcal/g synthesis cost of glycogen
$\rho_F$ 9.4 kcal/g energy density of fat
$\rho_C$ 4.2 kcal/g energy density of glycogen
$\rho_P$ 4.7 kcal/g energy density of protein
The following model constants are from Hall, (Hall, DOI: 10.1152/ajpendo.00559.2009):
$\beta_C$ 0.95 dimensionless adjustment factor for digestion and absorption of ingested carbohydrate
$\beta_F$ 0.96 dimensionless adjustment factor for digestion and absorption of ingested fat
$\beta_P$ 0.90 dimensionless adjustment factor for digestion and absorption of protein
The following model constants are from Livesey, (Livesey, G. and M. Elia. Estimation of energy expenditure, net carbohydrate utilization, and net fat oxidation and synthesis by indirect calorimetry: evaluation of errors with special reference to the detailed composition of fuels. American Journal of Clinical Nutrition. April 1988; 47(4):608-628.):

Hc 5.047 kcal·Liter$^{-1}$ heat equivalent of oxygen for carbohydrate

Hf 4.686 kcal·Liter$^{-1}$ heat equivalent of oxygen for fat Hp 4.656 kcal·Liter$^{-1}$ heat equivalent of oxygen for protein The following model constants are from Simonson, (Simonson, D. C. and R. A. DeFronzo. Indirect calorimetry: methodological and interpretative problems. American Journal of Physiology-Endocrinology and Metabolism. March 1990; 258(3):E399-E412.):

Fs 2.32 Kcal/gram energy cost of lipid synthesis

Definitions

The daily change of the glycogen store for day k−1 is defined as:

$$\Delta G_k := G_k - G_{k-1};\quad\quad\text{Def. 1.}$$

The daily change of the fat store for day k−1 is defined as:

$$\Delta F_k := F_k - F_{k-1};\quad\quad\text{Def. 2.}$$

The daily change of the protein store for day k−1 is defined as:

$$\Delta P_k := P_k - P_{k-1};\quad\quad\text{Def. 3.}$$

The daily change of the glycogen store for day k is defined as:

$$\Delta G_{k+1} := G_{k+1} - G_k;\quad\quad\text{Def. 4.}$$

The daily change of the fat store for day k is defined as:

$$\Delta F_{k+1} := F_{k+1} - F_k;\quad\quad\text{Def. 5.}$$

The daily change of the protein store for day k is defined as:

$$\Delta P_{k+1} := P_{k+1} - P_k;\quad\quad\text{Def. 6.}$$

The daily change of the extracellular water mass for day k−1 is defined as:

$$\Delta ECW_k := ECW_k - ECW_{k-1};\quad\quad\text{Def. 7.}$$

The daily change of the intracellular water mass for day k−1 is defined as:

$$\Delta ICW_k := ICW_k - ICW_{k-1};\quad\quad\text{Def. 8.}$$

The total energy expenditure is calculated from the resting metabolic rate and the physical activity energy expenditure as:

$$TEE_k := RMR_k + PAE_k;\quad\quad\text{Def. 9.}$$

The bone mass is calculated as in Hall 2010 (Hall, DOI: 10.1152/ajpendo.00559.2009):

$$BM = 0.04 \cdot BW_0;\quad\quad\text{Def. 10.}$$

The extracellular protein mass is calculated with the following regression equation from Hall, (Hall, DOI: 10.1152/ajpendo.00559.2009) after adaptation from Wang, (Wang Z, Shen W, Kotler D P, Heshka S, Wielopolski L, Aloia J F, Nelson M E, Pierson R N Jr, Heymsfield S B. Total body protein: a new cellular level mass and distribution prediction model. The American Journal of Clinical Nutrition 78: 979-984, 2003.):

$$ECP := 0.732 \cdot BM + 0.01087 \cdot ECW_0;\quad\quad\text{Def.11.}$$

The lean body mass is calculated from brain mass, extracellular protein, extracellular water mass, intracellular water mass, protein mass, and glycogen mass as:

$$L_k := BM + ECP + ECW_k + ICW_k + P_k + G_k;\quad\quad\text{Def. 12.}$$

The change of lean body mass is calculated from daily changes of extracellular water mass, intracellular water mass, protein mass, and glycogen mass as:

$$\Delta L_k := \Delta ECW_k + \Delta ICW_k + \Delta P_k + \Delta G_k;\quad\quad\text{Def. 13.}$$

The body weight is calculated from lean body mass and body fat mass as:

$$BW_k := L_k + F_k;\quad\quad\text{Def. 14.}$$

The daily change of body weight is calculated from daily change of lean body mass and body fat mass as:

$$\Delta BW_k := \Delta L_k + \Delta F_k;\quad\quad\text{Def. 15.}$$

The change of body weight is calculated from daily changes of extracellular water mass, intracellular water mass, fat mass, protein mass, and glycogen mass as:

$$\Delta BW_k := \Delta ECW_k + \Delta ICW_k + \Delta F_k + \Delta P_k + \Delta G_k;\quad\quad\text{Def. 16.}$$

The body cell mass is calculated from intracellular water mass, protein mass, glycogen mass, and brain mass as:

$$BCM_k := ICW_k + P_k + G_k - M_B;\quad\quad\text{Def. 17.}$$

The daily change of body cell mass is calculated from daily changes of intracellular water mass, protein mass, and glycogen mass as:

$$\Delta BCM_k := \Delta ICW_k + \Delta P_k + \Delta G_k;\quad\quad\text{Def. 18.}$$

The total energy expenditure $TEE_k$ is calculated from rate of carbohydrate oxidation, rate of fat oxidation, rate of protein oxidation, and indirectly calculated correction factor for unidentified energy losses or gains:

$$TEE_k := CarbOx_k + FatOx_k + ProtOx_k + \hat{\varphi}_k;\quad\quad\text{Def. 19.}$$

The retained or released energy is calculated from the daily change of the glycogen store, the daily change of the fat store and the daily change of the protein store as:

$$RRE_k := \rho_C \cdot \Delta G_{k+1} + \rho_F \cdot \Delta F_{k+1} \rho_P \cdot \Delta P_{k+1};\quad\quad\text{Def. 20.}$$

The retained or released energy is calculated from utilized carbohydrate intake, utilized fat intake, utilized protein intake, and the total energy expenditure as:

$$RRE_k := CI_k + FI_k + PI_k - TEE_k;\quad\quad\text{Def. 21.}$$

The total 24 h excretion of nitrogen is calculated from rate of protein oxidation and gluconeogenesis from protein as:

$$Nexcr_k := (6.25 \cdot \rho_P)^{-1} \cdot (ProtOx_k + GNGP_k);\quad\quad\text{Def. 22.}$$

The energy needed for fat synthesis is calculated during net fat loss:

$$EFs_k := 0;\quad\quad\text{Def. 23.}$$

The energy needed for fat synthesis is calculated during net fat loss:

$$EFs_k := (F_s - r_G) \cdot \Delta F_{k+1};\quad\quad\text{Def. 24.}$$

The rate of de novo lipogenesis is calculated by using the following identity calculation:

$$DNL_k := DF_k;\quad\quad\text{Def. 25.}$$

The estimated rate of endogenous lipolysis with calibration is calculated using the following calculation:

$$DF_k := \frac{\hat{D}_F^{NEW}}{\hat{D}_F} \cdot \hat{\mu}_k \cdot DF_k;\quad\quad\text{Def. 26}$$

The estimated gluconeogenesis from protein with calibration is calculated using the following calculation:

$$\widehat{GNGP_k} := \frac{\hat{GNG}_P^{NEW}}{\hat{GNG}_P} \cdot \hat{v}_k \cdot GNGP_k;. \qquad \text{Def. 27}$$

The molecular weight ratio free fatty acid to triglyceride is calculated as:

$$r_{FFA} := \frac{3 \cdot M_{FFA}}{M_{TG}};. \qquad \text{Def. 28}$$

The molecular weight and energy density ratio glycerol to triglyceride is calculated as:

$$r_{GF} := \frac{\rho_C \cdot M_G}{\rho_F \cdot M_{TG}};. \qquad \text{Def. 29}$$

The molecular weight ratio glycerol to triglyceride is calculated as:

$$r_G := \frac{\rho_C \cdot M_G}{M_{TG}};. \qquad \text{Def. 30}$$

The body composition vector with elements of size of macronutrient stores glycogen, fat and protein for day k is constructed as:

$$BC_k := (G_k F_k P_k)^T; \qquad \text{Def. 31}$$

The utilized energy intake vector with elements of daily metabolized macronutrient intake carbohydrate, fat and protein for day k is constructed as:

$$EI_k := (CI_k FI_k PI_k)^T; \qquad \text{Def. 32}$$

The macronutrient oxidation vector with elements of energy content obtained after oxidation of carbohydrate, fat and protein for day k is constructed as:

$$Ox_k := (CarbOx_k FatOx_k ProtOx_k)^T; \qquad \text{Def. 33}$$

Change of body composition vector is constructed as:

$$\Delta BC_k := (\Delta G_k \Delta F_k \Delta P_k)^T; \qquad \text{Def. 34}$$

Change of body composition vector is calculate from body composition vectors of day k+1 and body composition vectors of day k as:

$$\Delta BC_{k+1} := BC_{k+1} - BC_k; \qquad \text{Def. 35}$$

Change of the estimated indirectly calculated body composition vector on day k+1 is constructed from the estimated indirectly calculated glycogen mass, fat mass, and protein mass on day k+1 as:

$$\Delta \widehat{BC}_{k+1}^* := (\Delta \hat{G}_{k+1}^* \Delta \hat{F}_{k+1}^* \Delta \hat{P}_{k+1}^*)^T; \qquad \text{Def. 36}$$

The constant matrix of the Measurement Model of Body Composition Change from Lean-Fat-Protein is construed as:

$$MNB := \begin{pmatrix} 1 & 0 & 1 \\ 0 & 1 & 0 \\ 0 & 0 & 1 \end{pmatrix};. \qquad \text{Def. 37}$$

The constant matrix of the Measurement Model of Body Composition Change from Lean-Fat-Resting Metabolic Rate:

$$MRB := \begin{pmatrix} 1 & 0 & 1 \\ 0 & 1 & 0 \\ \eta_G & \eta_F & \eta_P \end{pmatrix};. \qquad \text{Def. 38}$$

The energy constant matrix of the Retained or Released Energy Model of the Human Energy Metabolism:

$$Mc := \begin{pmatrix} \rho_C & \rho_F & \rho_P \\ \eta_G & \eta_F & \eta_P \\ 0 & 0 & \rho_P \end{pmatrix};. \qquad \text{Def. 39}$$

Description—First Embodiment

FIG. 1. illustrates how the measurements of a device for body composition and hydration status analysis 109 flows into a method 130 for dynamic indirect individualized measurement of components of the human energy metabolism, and this method 130 is illustrated in detail in the flowchart in FIG. 5.

A human subject 105 undergoes a body composition change of his or her glycogen store, fat store, and protein store on an examined day k. A total energy expenditure 101 is produced on day k and leaves the human subject 105 on day k. Energies enter the human subject 105 in the form of the ingested carbohydrate intake 102, fat intake 103, and protein intake 104 on day k. A device for body composition and hydration status analysis 109 measures resistance directly at multiple frequencies and I extrapolate indirectly to zero frequency and infinite frequency on day k 106. The same device for body composition and hydration status analysis 109 measures the extracellular water mass on day k 126, the intracellular water mass on day k 127, and the change of lean body mass and fat mass on day k 107. The same device 109 can optionally measure acute change of extracellular water mass and intracellular water mass 108. A measurement of physical activity energy expenditure 110 is required on day k. Optional measurements of ingested energy in the form of carbohydrate 111, fat 112, and protein 113 are taken on day j for calibration purposes. An optional measurement of resting metabolic rate 114 is taken on day j for calibration purposes. An optional measurement of nitrogen excretion 115 is taken on day j for calibration purposes and to indirectly measure the daily gluconeogenesis. An optional measurement of the rate of endogenous lipolysis 116 is taken on day j for calibration purposes and to indirectly measure the daily lipolysis. The method for dynamic indirect individualized measurement of components of the human energy metabolism 130 comprises a Self Correcting Model of the Utilized Energy Intake 131, a Self Adaptive Model of the Human Energy Metabolism 132, and a calculation of the components of the human energy metabolism 133. The Self Correcting Model of the Utilized Energy Intake 131 estimates the utilized energy intake, defined as the daily utilized energy of carbohydrate, fat, and protein caloric intake 119. The Self Adaptive Model of the Human Energy Metabolism 132 estimates the daily change of body composition, defined as the change of glycogen store, fat store, and protein store 118. The calculation of the components of the human energy metabolism 133 provides the macronutrient oxidation rate results, defined as the daily rate of carbohydrate oxidation, fat oxidation, and protein oxidation 120; daily resting metabolic rate 121; daily unknown forms of energy losses or gains 122; daily rate of endogenous lipolysis 123; daily nitrogen excretion 124; and daily gluconeogenesis from protein 125.

FIG. 2. illustrates an interface electrical connection between the human subject 105 and measuring points 1, 208, measuring point 3, 211, measuring point 4, 213, and measuring point 5, 215. The same figure also shows the lumped circuit diagram equivalent of the human subject 105 connected to nodal junctions 216 and 217. The lumped circuit diagram is made up of the resistance at zero frequency 205 connected parallel to the serially connected membrane capacitance 207 and resistance at infinite frequency 206. Nodal junction 216 is also connected to earth potential 202 through stray capacitance 1, 204. Nodal junction 216 is also connected to measuring point 1, 208 through excitation electrode resistance 1, 209, and to measuring point 3, 211, through Sensory electrode resistance 1, 210. Nodal junction 217 is also connected to earth potential 202 through stray capacitance 2, 203. Nodal junction 217 is also connected to measuring point 5, 215 through excitation electrode resistance 2, 214 and to measuring point 4, 213 through sensory electrode resistance 2, 212. I model the human impedance with a Cole circuit model consisting of a resistance at zero frequency 205 connected parallel to the serially connected membrane capacitance 207 and resistance at infinite frequency 206. This Cole circuit model provides the impedance of the human subject 105.

FIG. 3. illustrates an input logic circuit connecting measuring point 1, 208, measuring point 3, 211, measuring point 4, 213, and measuring point 5, 215, which are in close proximity to the human subject 328, with measuring point 1, 208, measuring point 3, 211, measuring point 4, 213, measuring point 5, 215, and measuring point 6, 325, inside of a device for body composition and hydration status analysis 327. Measuring point 1, 208, in close proximity to the human subject 328, is connected to measuring point 1, 208, inside of the device for body composition and hydration status analysis 327, through on and off switch 14, 310. Measuring point 1, 208, in close proximity to the human subject 328, is also connected to measuring point 6, 325, inside of the device for body composition and hydration status analysis 327, through reference resistance 1, 324. Measuring point 3, 211, in close proximity to the human subject 328, is directly connected to measuring point 3, 211, inside of a device for body composition and hydration status analysis 327. Measuring point 4, 213, in close proximity to the human subject 328, is directly connected to measuring point 4, 213, inside of a device for body composition and hydration status analysis 327. Measuring point 5, 215, in close proximity to the human subject 328, is connected to measuring point 5, 215, inside of the device for body composition and hydration status analysis 327, through on and off switch 13, 322. Measuring point 5, 215, in close proximity to the human subject 328, is connected to measuring point 2, 320, inside of the device for body composition and hydration status analysis 327, through reference resistance 2, 321. Measuring point 5, 215, in close proximity to the human subject 328, is connected to measuring point 0, 319, inside of the device for body composition and hydration status analysis 327, through on and off switch 7, 312.

Measuring points 1, 3, 4, and 5, 208, 211, 213, and 215, respectively, in close proximity to the human subject 328, are connected through on and off switches 1-6, 306, 307, 305, 309, 308, and 311, respectively. Measuring point 1, 208, is connected to measuring point 3, 211, through on and off switch 2, 307. Measuring point 1, 208, is connected to measuring point 5, 215, through on and off switch 4, 309. Measuring point 1, 208, is connected to measuring point 4, 213, through on and off switch 5, 308. Measuring point 3, 211, is connected to measuring point 4, 213, through on and off switch 1, 306. Measuring point 3, 211, is connected to measuring point 5, 215, through on and off switch 6, 311. Measuring point 4, 213, is connected to measuring point 5, 215, through on and off switch 3, 305.

Measuring points 6, 1, 3, 4, 5, 2, and 0, 325, 208, 211, 213, 215, 320, and 319, respectively, inside of the device for body composition and hydration status analysis 327, are connected through on and off switches 7-15, 312, 313, 314, 315, 316, 317, 322, 310, and 323, respectively. Measuring point 0, 319, is connected to earth potential 202. Measuring point 6, 325, is connected to measuring point 0, 319, through reference resistance 1, 324, and on and off switch 8, 313. Measuring point 6, 325, is also connected to earth potential 202 through on and off switch 15, 323. Measuring point 1, 208, is connected to measuring point 0, 319, through on and off switch 14, 310, and on and off switch 8, 313. Measuring point 3, 211, is connected to measuring point 0, 319, through on and off switch 9, 314. Measuring point 4, 213, is connected to measuring point 0, 319, through on and off switch 10, 315. Measuring point 5, 215, is connected to measuring point 0, 319, through on and off switch 11, 316. Measuring point 2, 320, is connected to measuring point 0, 319, through on and off switch 12, 317.

FIG. 4. illustrates the measuring circuit of the first embodiment to determine the impedance of a human subject at various frequencies. The measuring circuit consists of the following elements in this order: connecting element 427; M6 or measuring point 6, 325; connecting element 428; reference resistance 1, 324; connecting element 429; M1 or measuring point 1, 208; connecting element 419; current excitation electrode 1, 410; connecting element 420; impedance of the human subject at various frequencies consisting of resistance and reactance, 105; connecting element 421; current excitation electrode 2, 408; connecting element 422; M5 or measuring point 5, 215; connecting element 423; reference resistance 2, 321; connecting element 424; M2 or measuring point 2, 320; connecting element 425; current source 2, 404; connecting element 426, which is also connected to earth potential 202; current source 1, 403; and again connecting element 427.

The current source driving means consists of a first in first out memory 401 and a digital-analog converter 402, which are connected with each other. The first in first out memory 401 is connected to the microcontroller unit 412 also containing memory means and a six-channel programmable gain instrumentation amplifier and filtering circuit. The digital-analog converter 402 is connected 431 to current source 1, 403, and is also connected 430 to current source 2, 404.

M1 or measuring point 1, 208, is between reference resistance 1, 324, and current excitation electrode 1, 410, on the measuring circuit and is also connected to M1 or measuring point 1 input 208 inside the microcontroller unit 412. M2 or measuring point 2, 320, is between current source 2, 404, and reference resistance 2, 321, on the measuring circuit and is also connected to M2 or measuring point 2 input 320 inside the microcontroller unit 412. M3 or measuring point 3, 211, is connected to voltage sensing electrode 1, 415, and is also connected to M3 or measuring point 3 input 211 inside the microcontroller unit 412. M4 or measuring point 4, 213, is connected to voltage sensing electrode 2, 418, and is also connected to M4 or measuring point 4 input 213 inside the microcontroller unit 412. M5 or measuring point 5, 215, is between current excitation electrode 2, 408, and reference resistance 2, 321, on the measuring circuit and is also connected to M5 or measuring point 5 input 215 inside the microcontroller unit 412. M6 or measuring point 6, 325, is between reference resistance 1, 324, and current source 1, 403, on the measuring circuit and is also connected to M6 or measuring point 6 input 325 inside the microcontroller unit 412.

Voltage sensing electrode 1, 415, is between the human subject with its impedance at various frequencies 105 and M3 or measuring point 3, 211. Voltage sensing electrode 2, 418, is between the human subject with its impedance at various frequencies 105 and M4 or measuring point 4, 213. M0 or measuring point 0 input 319 inside the microcontroller unit 412 is connected to earth potential 202. The digital signal processor unit of the device for body composition and hydration status analysis 413 is connected to the microcontroller unit 412.

Operation—First Embodiment

The overview of the operation of the first embodiment of my apparatus and method for the analysis of change of body composition and hydration status and for dynamic indirect individualized measurement of components of the human energy metabolism is depicted on FIG. 1. The GLOSSARY lists the definitions of the upper indices, definitions of lower indices, signs for the estimated value and assigned variable, scalar variables, vector variables, matrix variables, dynamic system and process models, measurement models, and model constants and definitions used in my first embodiment.

The human subject's metabolism 105 takes up energy in the form of the ingested carbohydrate intake 102, fat intake 103, and protein intake 104 on day k. The metabolism uses this energy intake; the human subject 105 undergoes body composition change of his or her glycogen store, fat store, and protein store on an examined day k; and a total energy expenditure 101 is produced. My apparatus for the analysis of change of body composition and hydration status 109 measures resistance directly at multiple frequencies and I extrapolate indirectly to zero frequency and infinite frequency on day k 106. Using these results the same device 109 measures the extracellular water mass 126, the intracellular water mass 127, the change of lean body mass, and change of fat mass on day k 107. The extracellular water mass and intracellular water mass 107 are calculated as in Eq. 148. and Eq. 149, respectively, in process 30, FIG. 5. The change of lean body mass and change of body fat mass 107 are calculated as in Eq. 152. and Eq. 153, respectively, in process 30, FIG. 5. The same device 109 can optionally measure acute change of extracellular water mass and intracellular water mass 108. The acute change of extracellular and intracellular water mass 108 are calculated as in Eq. 163. and Eq. 164, respectively, in process 34, FIG. 5. A measurement of physical activity energy expenditure 110 is required on day k. Optional measurements of ingested energy in the form of carbohydrate 111, fat 112, and protein 113 are taken on day j for calibration purposes. An optional measurement of resting metabolic rate 114 is taken on day j for calibration purposes. An optional measurement of nitrogen excretion 115 is taken on day j for calibration purposes to indirectly measure daily gluconeogenesis. An optional measurement of the rate of endogenous lipolysis 116 is taken on day j for calibration purposes to indirectly measure daily lipolysis. The method for dynamic indirect individualized measurement of components of the human energy metabolism 130 comprises a Self Correcting Model of the Utilized Energy Intake 131, a Self Adaptive Model of the Human Energy Metabolism 132, and a calculation of the components of the human energy metabolism 133. The Self Correcting Model of the Utilized Energy Intake 131 estimates the utilized energy intake, defined as the daily utilized energy of carbohydrate, fat, and protein caloric intake 119. The Self Adaptive Model of the Human Energy Metabolism 132 estimates the daily change of body composition, defined as the change of glycogen store, fat store, and protein store 118. The calculation of the components of the human energy metabolism 133 provides the macronutrient oxidation rate results, defined as the daily rate of carbohydrate oxidation, fat oxidation, and protein oxidation 120; daily resting metabolic rate 121; daily unknown forms of energy losses or gains 122; daily rate of endogenous lipolysis 123; daily nitrogen excretion 124; and daily gluconeogenesis from protein 125.

The overview of the operation of one embodiment of my apparatus for the analysis of change of body composition and hydration status 109 is depicted on FIG. 2, FIG. 3, and FIG. 4. I measure the passive circuit elements of the Cole circuit model representing the impedance of the human subject 105. The Cole circuit model consists of a resistance at zero frequency 205 connected parallel to the serially connected membrane capacitance 207 and resistance at infinite frequency 206. At zero frequency, the Cole circuit model consists of a resistance at zero frequency 205 and at infinite frequency it reduces to a parallel circuit of a resistance at zero frequency 205 connected parallel to a resistance at infinite frequency 206. For higher frequencies than zero and lower frequencies than the infinite frequency, the Cole circuit model has properties of a complex impedance with a resistance and reactance value. I perform measurements at a multitude of discrete preset frequencies from 1 kilohertz to 1 megahertz. At these frequencies the presence of a membrane capacitance 207 is also measurable and 205, 206, and 207 is detected as a specific resistance and reactance value of an impedance 105. For each preset frequency, a particular impedance is found. The digital signal processor unit 413 calculates 205 and 206 by fitting the Cole circuit model to the measured impedance values. In the measuring environment, other passive elements with electrical properties are present as well. These are the stray capacitance 1, 204, the stray capacitance 2, 203 the excitation electrode resistance 1, 209, the excitation electrode resistance 2, 214, the sensory electrode resistance 1, 210, and the sensory electrode resistance 2, 212. To determine the value of the unknown circuit elements, an excitation current of sinusoidal form flows through the unknown circuit elements and I take voltage signal measurements at the same time at six measuring points 208, 320, 211, 213, 215, and 325. The excitation current comes from current sources 1 and 2, 403 and 404, where one of the two current sources injects the excitation current and the other sinks the current. The injecting and sinking function alternates between the current sources 403 and 404 every half period of the excitation frequency. I measure the voltage signal along the path of the measuring circuit, which starts off at earth potential 202, continues with 426, 403, 427, 325, 428, 324, 429, 208, 419, 410, 420, 209, and 216, branches off to 204, 202, 222, 205, and 221, and 218, 207, 219, 206, 205, and 220, merges at 217, branches off to 203, 202, 214, 421, 408, 422, 215, 423, 321, 424, 320, 425, 404, and ends at 202. I use an input logic circuit 327 and 328 to isolate or short circuit or leave unchanged preselected parts of the measurement circuit. The determination of the unknown lumped passive elements 105, 203, 204, 209, 210, 212, and 214 occurs with appropriate setting of the input logic circuit 327 and 328. Before each measurement cycle I measure both offset voltage and voltage noise at six measuring points 208, 320, 211, 213, 215, and 325. These results are used later for elimination of offset error and minimization of voltage noise. The measurement cycle has two steps. With step one I determine the value of stray capacitance 1, 204, excitation electrode resistance 1, 209, sensory electrode resistance 1, 210, stray capacitance 2, 203, excitation electrode resistance 2, 214, and sensory electrode resistance 2, 212, using the input logic circuit 328 and 327 with appropriate setting of switches 1-15, 306, 307, 305, 309, 308, 311, 312, 313, 314, 315, 316, 317, 322, 310, and 323, respectively, and applying Ohm's law and Kirchhoff's first and second law.

In the second step, I determine the unknown impedance or resistance and reactance of the human subject 105 at a preset frequency by using the input logic circuit 328 and 327 with appropriate setting of switches 1-15, 306, 307, 305, 309, 308, 311, 312, 313, 314, 315, 316, 317, 322, 310, and 323, respectively, and applying Ohm's law and Kirchhoff's first and second law. The magnitude of the offset voltage and amplitude as well as the phase angle of the voltage signal from measuring point 6, 326, measuring point 1, 208, and measuring point 3, 211, are referenced to reference resistance 1, 324, and from measuring point 2, 320, measuring point 5, 215, and measuring point 4, 213, are referenced to reference resistance 2, 321, respectively. The measurement of resistance and reactance of the human subject at each preset frequency starts with loading a sine function of at least 16 wave lengths to a first in first out memory 401 by a microcontroller unit 412. Upon a trigger by the microcontroller unit 412, the train of at least 16 sine waves is sent to a digital-analog converter 402 at a predetermined rate by the microcontroller unit 412. The digital-analog converter 402 generates an excitation pattern with opposing phase for current source 1, 403, and current source 2, 404. Programmable gain instrumentation amplifiers within the microcontroller unit 412 pick up the voltage signals at the six measuring points 208, 320, 211, 213, 215, and 325 and amplify and filter the signal adjusted by the microcontroller within the microcontroller unit 412. The microcontroller unit 412 performs analog-digital conversion of the amplified and filtered voltage signal from the six measuring points 208, 320, 211, 213, 215 and 325. The microcontroller unit 412 then sends the signal first to the memory means of the microcontroller unit 412 and upon demand sends the signal to a digital signal processor unit 413. The digital signal processor unit 413 uses a sine wave function fitting algorithm to determine amplitude, phase, and offset of the digitized, amplified, and filtered voltage signal from the six measuring points 208, 320, 211, 213, 215 and 325 by minimizing the sum of the square of the deviations between the measured signal and a mathematical sine function of known frequency. The errors of the filtered voltage signal, defined as the difference between the predicted and measured digitalized, amplified, and filtered voltage signal from the six measuring points 208, 320, 211, 213, 215 and 325, are used for measurement of quality and to indicate whether a repeat measurement cycle is needed.

The digital processor unit 413 performs a non-linear curve fitting algorithm of the Cole circuit model to the measured resistances and reactances of human subject 105 at preset frequencies and extrapolates the best fitting Cole circuit model curve to zero and infinite frequency to obtain resistance of the human subject at zero and infinite frequency. I use the sum of the square of the deviations between Cole circuit model predicted and actually measured impedance values to measure quality and reliability of my apparatus' functioning.

FIG. 5. shows the detailed overview of the operation of the first method for the analysis of change of body composition and hydration status and for dynamic indirect individualized measurement of components of the human energy metabolism. The method starts at 1. The calculation for subsequent days merges with the start at 2. The algorithm branches off at decision point 3.

If this is an initiation day then the process continues at 5. The index variable for the day k is set to zero as expressed in Eq. 0. The initial values are entered for body cell mass $BCM_0$, extracellular water mass $ECW_0$, lean body mass $L_0$, intracellular water mass $ICW_0$, glycogen mass $G_0$, fat mass $F_0$, protein mass $P_0$, ingested carbohydrate intake $CI_0^\sim$, ingested fat intake $FI_0^\sim$, ingested protein intake $PI_0^\sim$, estimated correction factor for de novo lipogenesis $\mu_0$, estimated correction factor for gluconeogenesis from amino acids $\hat{v}_0$, and estimated correction factor for unidentified energy losses or gains $\hat{\varphi}_0$.

If this is not an initiation day then the process continues at 4 where the index variable for day k is set to a chosen value.

The algorithm branches off at decision point 6.

If this is a calibration day and the ingested macronutrient calories are available, the process continues at 7 with Eq. 1. to Eq. 3, which calculate the utilized macronutrient energy intake vector (Hall, DOI: 10.1152/ajpendo.00559.2009) from the ingested macronutrient intake. The process continues at 9.

At process 9, Eq. 4. calculates the rate of proteolysis and Eq. 5. calculates the rate of glycogenolysis. Eq. 6. calculates the fat store dependent coefficient for rate of endogenous lipolysis on day k. Eq. 7. calculates the carbohydrate intake dependent coefficient for rate of endogenous lipolysis. Eq. 8. calculates the bias for rate of endogenous lipolysis on day k. Eq. 9. calculates the rate of endogenous lipolysis on day k. Eq. 10. calculates the carbohydrate intake dependent coefficient for rate of de novo lipogenesis. Eq. 11. calculates the glycogen store dependent coefficient for rate of de novo lipogenesis on day k. Eq. 12. calculates bias for rate of endogenous lipolysis on day k. Eq. 13. calculates the rate of de novo lipogenesis. Eq. 14. calculates the rate of glycerol gluconeogenesis. Eq. 15. calculates the protein store dependent coefficient for gluconeogenesis from protein. Eq. 16. calculates the carbohydrate intake dependent coefficient for gluconeogenesis from protein. Eq. 17. calculates the protein intake dependent coefficient for gluconeogenesis from protein. Eq. 18. calculates the bias for gluconeogenesis from protein. Eq. 19. calculates the rate of gluconeogenesis from protein. Eq. 20. calculates the glycerol 3-phosphate synthesis. Eq. 21. calculates the resting metabolic rate with a filtering formula on day k. Eq. 22. calculates the indirectly calculated total energy expenditure from the resting metabolic rate with the filtering formula on day k and directly measured physical activity energy expenditure. Eq. 23. calculates the 24 hour nitrogen excretion from utilized protein intake on day k and the daily change of the protein store for day k–1. The process continues at 16.

If at decision point 6 this is not a calibration day and the ingested macronutrient calories are not available, the process continues at decision point 8.

If there is no trajectory value $\Delta BC_{k+1}^{TR*}$, called the change of trajectory of indirectly calculated change of body composition vector of day k, available for $\Delta BC^*_{k+1}$, called the indirectly calculated change of body composition vector of day k, at decision point 8, then the algorithm continues with process 10.

At process 10, Eq. 24. shows the calculation of the rate of proteolysis on day k. Eq. 25. calculates the rate of glycogenolysis on day k. Eq. 26. calculates the fat store dependent coefficient for the rate of endogenous lipolysis on day k. Eq. 27. calculates the carbohydrate intake dependent coefficient for the rate of endogenous lipolysis on day k. Eq. 28. calculates the bias for the rate of endogenous lipolysis on day k. Eq. 29. calculates the rate of endogenous lipolysis on day k. Eq. 30. calculates the carbohydrate intake dependent coefficient for the rate of de novo lipogenesis on day k. Eq. 31. calculates the glycogen store dependent coefficient for the rate of de novo lipogenesis on day k. Eq. 32. calculates the bias for the rate of endogenous lipolysis on day k. Eq. 33. calculates the rate of de novo lipogenesis on day k. Eq. 34. calculates the rate of glycerol gluconeogenesis on day k. Eq. 35. calculates the protein store dependent coefficient for gluconeogenesis from protein on day k. Eq. 36. calculates the carbohydrate intake dependent coefficient for gluconeogenesis from protein on day k. Eq. 37. calculates the protein intake dependent coefficient for gluconeogenesis from protein on day k. Eq. 38. calculates the bias for gluconeogenesis from protein on day k. Eq. 39. calculates the rate of gluconeogenesis from protein on day k. Eq. 40. calculates a part of the resting metabolic rate which is independent of the body composition vector changes and the time-varying constant energy expenditure on day k. Eq. 41. calculates the resting metabolic rate with predictive formula on day k. Eq. 42. calculates a part of the resting metabolic rate which is dependent on the utilized carbohydrate intake on day k. Eq. 43. calculates a part of the resting metabolic rate which is dependent on the utilized fat intake on day k. Eq. 44. calculates a part of the resting metabolic rate which is dependent on the utilized protein intake on day k. The process continues at 11.

At process 11, Eq. 45. constructs the energy constant matrix of the Retained or Released Energy Model of the Human Energy Metabolism on day k. Eq. 46. constructs the time varying utilized energy intake coupling matrix in the Retained or Released Energy Model of the Human Energy Metabolism on day k. Eq. 47. constructs the indirectly calculated bias vector of the Retained or Released Energy Model of the Human Energy Metabolism on day k. Eq. 48. calculates the utilized energy intake vector indirectly with the Measurement Model of the Utilized Energy Intake from body composition vector change on day k, which I obtain either from Eq. 117. or Eq. 119. where I obtain the lean body mass change and fat mass change from 107, which is part of 109, the device and method for body composition and hydration status analysis. Eq. 49. assigns the value of the utilized carbohydrate intake indirectly calculated by the Measurement Model of the Utilized Energy Intake from body composition vector change on day k to the variable for the utilized carbohydrate intake on day k. Eq. 50. assigns the value of the utilized fat intake indirectly calculated by the Measurement Model of the Utilized Energy Intake from body composition vector change on day k to the variable for the utilized fat intake on day k. Eq. 51. assigns the value of the utilized protein intake indirectly calculated by the Measurement Model of the Utilized Energy Intake from body composition vector change on day k to the variable for the utilized protein intake on day k. The process continues at process 9.

If there is a trajectory value $\Delta BC_{k+1}^{TR*}$, called the change of trajectory of indirectly calculated change of body composition vector of day k, available for $\Delta BC^*_{k+1}$, called the indirectly calculated change of body composition vector of day k, at decision point 8, then the algorithm continues with process 12.

At process 12, Eq. 52. shows the calculation of the rate of proteolysis on day k−1. Eq. 53. calculates the rate of glycogenolysis on day k−1. Eq. 54. calculates the fat store dependent coefficient for the rate of endogenous lipolysis on day k−1. Eq. 55. calculates the carbohydrate intake dependent coefficient for the rate of endogenous lipolysis on day k−1. Eq. 56. calculates the bias for the rate of endogenous lipolysis on day k−1. Eq. 57. calculates the rate of endogenous lipolysis on day k−1. Eq. 58. calculates the carbohydrate intake dependent coefficient for the rate of de novo lipogenesis on day k−1. Eq. 59. calculates the glycogen store dependent coefficient for the rate of de novo lipogenesis on day k−1. Eq. 60. calculates the bias for the rate of endogenous lipolysis on day k−1. Eq. 61. calculates the rate of de novo lipogenesis on day k−1. Eq. 62. calculates the rate of glycerol gluconeogenesis on day k−1. Eq. 63. calculates the protein store dependent coefficient for gluconeogenesis from protein on day k−1. Eq. 64. calculates the carbohydrate intake dependent coefficient for gluconeogenesis from protein on day k−1. Eq. 65. calculates the protein intake dependent coefficient for gluconeogenesis from protein on day k−1. Eq. 66. calculates the bias for gluconeogenesis from protein on day k−1. Eq. 67. calculates the rate of gluconeogenesis from protein on day k−1. Eq. 68. calculates a part of the resting metabolic rate which is independent of the body composition vector changes and the time-varying constant energy expenditure on day k−1. Eq. 69. calculates the resting metabolic rate with predictive formula on day k−1. Eq. 70. calculates a part of the resting metabolic rate which is dependent on the utilized carbohydrate intake on day k−1. Eq. 71. calculates a part of the resting metabolic rate which is dependent on the utilized fat intake on day k−1. Eq. 72. calculates a part of the resting metabolic rate which is dependent on the utilized protein intake on day k−1. The process continues at 13.

At process 13, Eq. 73. shows the calculation of rate of proteolysis on day k. Eq. 74. calculates the rate of glycogenolysis on day k. Eq. 75. calculates the fat store dependent coefficient for rate of endogenous lipolysis on day k. Eq. 76. calculates carbohydrate intake dependent coefficient for rate of endogenous lipolysis on day k. Eq. 77. calculates the bias for rate of endogenous lipolysis on day k. Eq. 78. calculates the rate of endogenous lipolysis on day k. Eq. 79. calculates the carbohydrate intake dependent coefficient for the rate of de novo lipogenesis on day k. Eq. 80. calculates the glycogen store dependent coefficient for the rate of de novo lipogenesis on day k. Eq. 81. calculates the bias for the rate of endogenous lipolysis on day k. Eq. 82. calculates the rate of de novo lipogenesis on day k. Eq. 83. calculates the rate of glycerol gluconeogenesis on day k. Eq. 84. calculates the protein store dependent coefficient for gluconeogenesis from protein on day k. Eq. 85. calculates the carbohydrate intake dependent coefficient for gluconeogenesis from protein on day k. Eq. 86. calculates the protein intake dependent coefficient for gluconeogenesis from protein on day k. Eq. 87. calculates the bias for gluconeogenesis from protein. Eq. 88. calculates the rate of gluconeogenesis from protein on day k. Eq. 89. calculates a part of the resting metabolic rate that is independent of the body composition vector changes and the time-varying constant energy expenditure on day k. Eq. 90. calculates the resting metabolic rate with a predictive formula on day k. Eq. 91. calculates a part of the resting metabolic rate which is dependent on the utilized carbohydrate intake on day k. Eq. 92. calculates a part of the resting metabolic rate which is dependent on the utilized fat intake on day k. Eq. 93. calculates a part of the resting metabolic rate which is dependent on the utilized protein intake on day k. The process continues at 14.

At process 14, Eq. 94. constructs the time varying utilized energy intake coupling matrix in the Retained or Released Energy Model of the Human Energy Metabolism on day k−1. Eq. 95. constructs the indirectly calculated bias vector of the Retained or Released Energy Model of the Human Energy Metabolism on day k−1. Eq. 96. constructs the time varying utilized energy intake coupling matrix in the Retained or Released Energy Model of the Human Energy Metabolism on day k. Eq. 97. constructs the indirectly calculated bias vector of the Retained or Released Energy Model of the Human Energy Metabolism on day k. Eq. 98. calculates the dynamic transition matrix in the Self Correcting Model of the Utilized Energy Intake on day k−1. Eq. 99. calculates dynamic coupling matrix in the Self Corrective Model of the Utilized Energy Intake on day k−1. Eq. 100. calculates the time varying bias vector in the Self Corrective Model of the Utilized Energy Intake on day k−1. Eq. 101. calculates the utilized energy intake vector, with the elements consisting of the daily metabolized macronutrient intake from carbohydrate, fat and protein on day k. I refer to Eq. 101. as the Linear Model of the Utilized Energy Intake, and this linear model also serves as the process model of the Self Correcting Model of the Utilized Energy Intake. Eq. 102. calculates the indirectly measured utilized energy intake vector on day k using the Retained or Released Energy Model of the Human Energy Metabolism, and I refer to Eq. 102. as the Measurement Model of the Utilized Energy Intake from body composition vector change. The input variable to Eq. 102. is the indirectly calculated change of body composition vector of day k, which I obtain either from Eq. 117. or Eq. 119. where I obtain the lean body mass change and fat mass change from 107, which is part of 109, the device and method for body composition and hydration status analysis. The process continues at process 15.

At process 15, the deviation of the estimated indirectly calculated utilized energy intake vector is evaluated with one of two optional equations, Eq. 103. or Eq. 104. Eq. 103. calculates the deviation of the estimated indirectly calculated utilized energy intake vector from the indirectly measured utilized energy intake vector on day k using the indirectly calculated change of body composition vector of day k and the Measurement Model of the Utilized Energy Intake. Eq. 104. calculates the deviation of the estimated indirectly calculated utilized energy intake vector from a trajectory using the change of trajectory of indirectly calculated change of body composition vector of day k and the Measurement Model of the Utilized Energy Intake. Eq. 105. implements the discrete time Kalman estimator with innovations representation for the daily utilized macronutrient energy intake vector using the Self Correcting Model of the Utilized Energy Intake with innovations representation. The Kalman gain matrix is calculated as in Grewal, (Grewal M. S. and A. P. Andrews. Kalman Filtering: Theory and Practice Using MATLAB. John Wiley & Sons, New Jersey. Third Ed.; September 2011, 136 pp.). Eq. 106. assigns the estimated indirectly calculated utilized energy intake vector by the Self Correcting Model of the Utilized Energy Intake on day k to the utilized energy intake vector vector with elements of daily metabolized macronutrient intake of carbohydrate, fat, and protein on day k. The process continues at 9.

At process 16, the macronutrient oxidation rates are calculated. Eq. 107. constructs the oxygen caloric heat equivalent constants matrix. Eq. 108. constructs the indirectly calculated heat energy equivalent vector on day k. Eq. 109. calculates the indirectly calculated macronutrient oxidation vector with the elements of energy content obtained after oxidation of carbohydrate, fat, and protein on day k. Eq. 110. assigns the values of the components of the macronutrient oxidation vector to variables of the calculated rate of carbohydrate oxidation, calculated rate of fat oxidation, and calculated rate of protein oxidation. The process continues at 17.

The process at 17 shows the process model of the Linear Extended Model of the Human Energy Metabolism. Eq. 111. calculates the daily energy of the glycogen store change for day k. Eq. 112. calculates the daily energy of fat store change for day k. Eq. 113. calculates the daily energy of protein store change for day k. The calculations in Eq. 111. to Eq. 113. are represented also in Eq. 114. with a matrix representation to calculate the change of body composition vector at the end of day k.

The algorithm branches off at decision point 18 and reunites again at 21. The measurement model can be either the Measurement Model of Body Composition Change from Lean-Fat-Protein as in Eq. 115. to Eq. 117. at process 19 or the Measurement Model of Body Composition Change from Lean-Fat-Resting Metabolic Rate as in Eq. 118. to Eq. 119. at process 20. Eq. 115. calculates daily change of the indirectly calculated body protein mass on day k. Eq. 116. calculates the change of the indirectly calculated lean-fat-protein vector of day k. Eq. 117. calculates the indirectly calculated change of body composition vector for day k, where I obtain the lean body mass change and fat mass change from 107, which is part of 109, the device and method for body composition and hydration status analysis. I refer to Eq. 117. as the Measurement Model of Body Composition Change from Lean-Fat-Protein. The algorithm continues at 21.

At process 20, Eq. 118. is the change of the indirectly calculated lean-fat-resting-metabolic-rate vector of day k. Eq. 119. calculates the indirectly calculated change of body composition vector for day k where I obtain the lean body mass change and fat mass change from 107, which is part of 109, the device and method for body composition and hydration status analysis. I refer to Eq. 119. as the Measurement Model of Body Composition Change from Lean-Fat-Resting-Metabolic-Rate. The algorithm continues at 21.

At process 21, the deviation of the estimated indirectly calculated change of body composition vector is evaluated with one of three optional equations, Eq. 120, Eq. 121, or Eq. 122. Eq. 120. calculates the deviation of the estimated indirectly calculated change of body composition vector of day k from the indirectly measured one using the Measurement Model of Body Composition Change from Lean-Fat-Protein. Eq. 121. calculates the deviation of the estimated indirectly calculated change of body composition vector of day k from the indirectly measured one using the Measurement Model of Body Composition Change from Lean-Fat-Resting-Metabolic-Rate. Eq. 122. calculates the deviation of the estimated indirectly calculated change of body composition vector from a trajectory on day k. Eq. 123. implements the discrete time variant Kalman estimator with innovations representation for the estimation of the indirectly calculated change of body composition of day k. In this equation, I use the Self Adaptive Model of the Human Energy Metabolism and innovations representation technique. The resulting estimates of the daily body composition change of day k allow for stochastic identification of the correction factors for de novo lipogenesis, gluconeogenesis from amino acids, and the correction factor for unidentified energy losses or gains, so that these model parameters become self adaptive. The Kalman gain matrices are calculated as in Grewal, (Grewal M. S. and A. P. Andrews. Kalman Filtering: Theory and Practice Using MATLAB. John Wiley & Sons, New Jersey. Third Ed.; September 2011, pp. 136.). The algorithm continues at 22.

At process 22, the estimators for the correction factors for de novo lipogenesis, gluconeogenesis from amino acids, and for unidentified energy losses or gains are shown in Eq. 124. to Eq. 126. Eq. 124. sets the a posteriori estimation of the correction factor for de novo lipogenesis of day k equal to the a priori estimation of the correction factor for de novo lipogenesis of day k+1. Eq. 125. sets the a posteriori estimation of the correction factor for gluconeogenesis of day k equal to the a priori estimation of the correction factor for gluconeogenesis of day k+1. Eq. 126. sets the a posteriori estimation of the correction factor for unidentified energy losses or gains of day k equal to the a priori estimation of the correction factor for unidentified energy losses or gains of day k+1. The measurement equations for the correction factors for de novo lipogenesis, gluconeogenesis from amino acids, and for unidentified energy losses or gains are calculated as in Eq. 127. to Eq. 129. The a posteriori estimation of the correction factors for de novo lipogenesis, gluconeogenesis from amino acids, and for unidentified energy losses or gains is performed using the Kalman filter as in Eq. 130. to Eq. 132. The Kalman gains are calculated as a scalar problem as in Grewal, (Grewal M. S. and A. P. Andrews. Kalman Filtering: Theory and Practice Using MATLAB. John Wiley & Sons, New Jersey. Third Ed.; September 2011, pp. 140). The algorithm continues at 23.

The algorithm branches off at decision point 23.

If no calibrations are desired than the process continues at decision point 26.

If this is a calibration day j with known ingested carbohydrate, fat, and protein calories; a known calibration value for body composition vector; and a trajectory calculation for body composition vector changes is desired, then a smoothing procedure of the indirectly calculated body composition vector change is performed and the process continues at 24. I prefer optimal smoothers (Grewal M. S. and A. P. Andrews. Kalman Filtering: Theory and Practice Using MATLAB. John Wiley & Sons, New Jersey. Third Ed.; September 2011, pp. 183.). The process continues at 25.

At process 25, the trajectory calculation is performed. My first embodiment uses the smoothed values of the indirectly measured body composition vector. The time interval for the trajectory is day i, which is the day of the previous calibration, to day j, which is the day of the last calibration. The constraint is that the trajectory starts with a calibration value of day i and ends with a calibration value of day j for the body composition vector. Eq. 133. calculates the trajectory of the body composition vector from day i to day j using the results of the smoothing algorithm. Alternative methods of trajectory creation include using mathematical methods (Venkataraman, P. Applied Optimization with MATLAB Programming. March 2009; John Wiley & Sons, pp. 490) which express the function of the trajectory as a parametric curve. Eq. 134. calculates the trajectory of the body composition vector from day i to day j using a polynomial spline function. Eq. 135. calculates the trajectory of the body composition vector from day i to day j using a B spline function. Eq. 136. calculates the trajectory of the body composition vector from day i to day j using a Bezier function. The algorithm continues at 26.

The algorithm branches off at decision point 26.

If no calibrations for the adjustable coefficients to calculate extracellular water and intracellular water masses are needed, then the process continues at 29.

If a calibration procedure for the adjustable coefficients to calculate extracellular water and intracellular water masses is needed, then the process continues at 27 and reference values are generated first. The reference value for extracellular water mass on calibration day j is obtained from tabled values (Silva, DOI:10.1088/0967-3334/28/5/004) as shown in Eq. 137, where the values are dependent on weight, height, age, sex and race. The reference value for intracellular water mass on calibration day j is calculated in Eq. 140. (Jaffrin, DOI: 10.1016/j.medengphy.2008.06.009). The formula requires the body weight and the reference value for fat mass on calibration day j. The reference value for fat mass on calibration day j is obtained from the anthropomorphic determination of body fat as in Lean, (Lean, et al. Predicting body composition vector by densitometry from simple anthropometric measurements. American Journal of Clinical Nutrition, January 1996; 63(1):4-14.), as in Eq. 138. for men and Eq. 139. for women. Eq. 141. calculates the reference value for the lean body mass.

The calibration process proceeds to 28, where the adjustable coefficients to calculate extracellular water and intracellular water masses are estimated. Eq. 142. sets the a posteriori estimation of the adjustable coefficient to calculate extracellular water on calibration day i equal to the a priori estimation of the adjustable coefficient to calculate extracellular water on day j. Eq. 143. sets the a posteriori estimation of the adjustable coefficient to calculate intracellular water on calibration day i equal to a priori estimation of the adjustable coefficient to calculate intracellular water on day j. The measurement equations for the adjustable coefficients to calculate extracellular water and intracellular water masses are calculated as in Eq. 144. to Eq. 145. The a posteriori estimation of the adjustable coefficients to calculate extracellular water and intracellular water masses is performed using the Kalman filter as in Eq. 146. and Eq. 147. The Kalman gains are calculated as a scalar problem as in Grewal, (Grewal M. S. and A. P. Andrews. Kalman Filtering: Theory and Practice Using MATLAB. John Wiley & Sons, New Jersey. Third Ed.; September 2011, 140 pp.). The algorithm continues at 29.

The algorithm branches off at decision point 29. If no measurement of the body composition vector and daily change in body composition vector is needed, then the process continues at decision point 31.

If measurement of the body composition vector and daily change in body composition vector is needed, then these can be calculated at process 30. Eq. 148. calculates the extracellular water mass from the resistance extrapolated at zero frequency. Eq. 149. calculates the intracellular water mass from the resistance extrapolated at infinite frequency. The lean body mass is calculated with Eq. 150. (Jaffrin, DOI: 10.1016/j.medengphy.2008.06.009). The body fat mass is obtained by subtracting the lean body mass from body weight as in Eq. 151. The lean body change from one day to the next day is obtained by subtracting the previous day's lean body mass from the next day's lean body mass as in Eq. 152. The daily fat mass change is obtained by subtracting the daily change of lean body mass from the daily body weight change as in Eq. 153. The algorithm continues at 31.

The algorithm branches off at decision point 31. If no calibration procedure for the adjustable dynamic coefficients to calculate extracellular water and intracellular water mass changes is needed, then the process continues at decision point 33.

If a calibration procedure for the adjustable dynamic coefficients to calculate extracellular water and intracellular water mass changes is needed, then the process continues at 32.

At process 32, I perform a calibration procedure for the adjustable dynamic coefficients to calculate extracellular water mass and intracellular water mass changes. In calculating dynamic changes of extracellular water and intracellular water, I take advantage of the observation that the ratio of the extracellular and total body water is tightly regulated in normal physiology (Ellis K J, Wong W W (1998) Human hydrometry: comparison of multifrequency bioelectrical impedance with $^2H_2O$ and bromine dilution. J Appl Physiol 85(3): 1056-1062.). The ratio can be calculate using reference values on day j. The ratio of the extracellular and total body water is determined from reference extra cellular water and intracellular water mass as in Eq. 154.

For the calibration of the acute change of extracellular and intracellular water mass, a known change of the total water mass is needed in a relatively short period of time so as not to affect the body composition vector change. Vigorous perspiration or rapid hydration with fluid can be such a sentinel event when the body loses or gains a measurable weight in a short period of time without any significant change of the body composition. The ensuing body weight change, and equivalently, the total body water change from the beginning to the end of the sentinel event causes the hydration change. The indirectly calculated extracellular water change for this scenario can be calculated as in Eq. 155. Eq. 155. requires the knowledge of the total water change of the body which can be obtained by measuring the weight before and after a sentinel event and calculating the difference. The ensuing change of the intracellular water is calculated in Eq. 156. Eq. 157. sets the a posteriori estimation of the adjustable dynamic coefficient to calculate extracellular water on calibration day i equal to the a priori estimation of the adjustable dynamic coefficient to calculate extracellular water on day j. Eq. 158. sets the a posteriori estimation of the adjustable dynamic coefficient to calculate intracellular water on calibration day i equal to the a priori estimation of the adjustable dynamic coefficient to calculate intracellular water on day j. The measurement equations for the adjustable dynamic coefficients to calculate extracellular and intracellular water masses are calculated in Eq. 159. to Eq. 160. The a posteriori estimation of the adjustable dynamic coefficients to calculate extracellular and intracellular water masses is performed using the Kalman filter in Eq. 161. and Eq. 162. and the Kalman gains are calculated as a scalar problem as in Grewal, (Grewal M. S. and A. P. Andrews. Kalman Filtering: Theory and Practice Using MATLAB. John Wiley & Sons, New Jersey. Third Ed.; September 2011, page 140). The algorithm continues at decision point 33.

The algorithm branches off at decision point 33. If no measurement of acute change of hydration status is needed, then the process continues at decision point 35.

If measurement for acute change of hydration status is needed, then the process continues at 34. Eq. 163. calculates dynamic changes of extracellular water indirectly from resistance value changes before and after the acute event causing hydration status change using the resistance extrapolated at zero frequency before and after a sentinel event of hydration status change. Eq. 164. calculates dynamic changes of intracellular water indirectly from resistance value changes before and after the acute event causing hydration status change using the resistance extrapolated at infinite frequency before and after a sentinel event of hydration change. The process continues at decision point 35.

The algorithm branches off at decision point 35.

If no calibration procedure for the estimation of the time varying constant energy expenditure is needed, the process continues at 37.

If a calibration procedure for the estimation of the time varying constant energy expenditure is needed, then the process continues at 36. Eq. 165. sets the a posteriori estimation of the time varying constant energy expenditure of the previous calibration day i equal to the a priori estimation of the time varying constant energy expenditure of the last calibration day j. The measurement equation for the time-varying constant energy expenditure for calibration day j is calculated as in Eq. 166. In this equation, the components of the indirectly calculated body composition vector change are entered, taken from the day before the calibration day j. Next, the a posteriori estimation of the time-varying constant energy expenditure is performed using the Kalman filter as in Eq. 167, and the Kalman gains are calculated as a scalar problem as in Grewal, (Grewal M. S. and A. P. Andrews. Kalman Filtering: Theory and Practice Using MATLAB. John Wiley & Sons, New Jersey. Third Ed.; September 2011, page 140). The process continues at decision point 37.

At decision point 37, if no calibration procedure for the basal gluconeogenesis rate is needed, the process continues at process 38. If a new value for the basal gluconeogenesis rate after previous calibration on day j is available than an estimated gluconeogenesis from protein on day k with calibration can be calculated as in Eq. 170. by multiplying the new value for the basal gluconeogenesis rate after calibration on day j with the estimation of the correction factor for gluconeogenesis from amino acids on day k and the gluconeogenesis from protein on day k and dividing the result with the old basal gluconeogenesis rate before calibration. The process continues at decision point 40.

At decision point 37, if a calibration procedure for the basal gluconeogenesis rate is needed, then the process continues at 39. For this calibration procedure the measured nitrogen excretion on calibration day j is required. Eq. 168. calculates the indirectly measured correction factor for gluconeogenesis from amino acids on calibration day j by evaluating a ratio with the numerator being the product of six point twenty-five multiplied with the energy density of protein and multiplied with the measured nitrogen excretion on calibration day j minus the calculated rate of protein oxidation rate on day j, divided by the gluconeogenesis from protein on day j. The indirectly measured correction factor for gluconeogenesis from amino acids on calibration day j could be used for the process equation Eq. 125. allowing for calibrated estimation of the gluconeogenesis from protein. Eq. 169. calculates the new value for the basal gluconeogenesis rate after previous calibration on day j by adding up the product of six point twenty-five multiplied with the energy density of protein, and multiplied with the measured nitrogen excretion on calibration day j minus the calculated rate of protein oxidation rate on day j. The process continues at decision point 40.

At decision point 40, if no calibration procedure for baseline lipolysis rate is needed, then the process continues at 41. If a new value for the baseline lipolysis rate after previous calibration on day j is available than an estimated rate of endogenous lipolysis on day k with calibration can be calculated as in Eq. 173. by multiplying the new value for the baseline lipolysis rate after calibration on day j with the estimation of the correction factor for de novo lipogenesis on day k and the rate of endogenous lipolysis on day k and dividing the result by the old baseline lipolysis rate before calibration. The process continues at decision point 43.

At decision point 40, if a calibration procedure for baseline lipolysis rate is needed, then the process continues at 42. For the calibration procedure, the measured rate of endogenous lipolysis on calibration day j is required. Eq. 171. calculates the indirectly measured correction factor for de novo lipogenesis on calibration day j by calculating the ratio of the baseline lipolysis rate before calibration and the measured rate of endogenous lipolysis on calibration day j. The indirectly measured correction factor for de novo lipogenesis on calibration day j could be used for the process equation Eq. 124. allowing for calibrated estimation of the rate of endogenous lipolysis. Eq. 172. calculates the new value for the baseline lipolysis rate after previous calibration on day j by equating it with the measured rate of endogenous lipolysis on calibration day j. The process continues at decision point 43.

At process 43, preparations are made to proceed with calculations for the next day. Eq. 173. increases the index variable for day k by one. Eq. 174. calculates the time-varying constant energy expenditure on day k+1.

At process 44, the entire calculation for the next day can be performed by proceeding from 44 to 2.

CONCLUSION, RAMIFICATIONS, AND SCOPE

Thus, the reader will see that at least one embodiment of the apparatus and method for the analysis of the change of body composition and hydration status and for dynamic indirect individualized measurement of components of the human energy metabolism provides several advantages. The advantages of the apparatus are that it:
a. measures and corrects for stray capacitances,
b. minimizes input noise and reduces capacitances of connecting cables,
c. measures and eliminates offset voltage at six measuring points and reduces noise by hardware and software means at six measuring points,
d. provides high output resistance and low output reactance of the current sources,
e. minimizes noise due to analog-digital conversion,
f. provides information on performance and reliability of measurements, and
g. provides individualized measurements of the extracellular and intracellular water mass and fat and lean body mass.

The advantages of dynamic indirect individualized measurement are that it:
a. provides individualized self correcting and self adaptive modeling of the human energy metabolism,
b. provides real time calculation of components of the human energy metabolism,
c. allows for inverse calculations and for inferring unknown input data from output results,
d. allows for real time calculations in a freely moving human subject with the need for measurements only in 24 hour increments,
e. allows for dynamic serial measurements of the body composition change where the metabolic model is fitted to the measured data and by using error measurements of the model which becomes individualized and self adaptive,
f. allows for calculating the macronutrient oxidation rates,
g. allows for estimation of the utilized macronutrient intake,
h. allows for detecting the unknown part of the energy metabolism and the error of metabolic model estimations, and
i. allows for identification of parameters of lipid degradation and gluconeogenesis from protein.

While my above description contains many specificities, these should not be construed as limitations on the scope, but rather as an illustration of one presently preferred embodiment. For example, the apparatus can:
a. have a multiplicity of measuring circuits to allow segmental measurements of the parts of the human body,
b. take measurements continuously rather than just daily or intermittently.
c. accommodate complex lumped network models of the human body consisting of a multitude of resistances, capacitances, and inductances,
d. obtain measurements at a higher frequency than 1 megahertz,
e. measure the capacitances of the excitation electrodes and sensory electrodes, and
f. measure frequency dependent characteristics of the human tissue.

Further, the dynamic indirect individualized measurement method can, for example, be extended to measure dynamically:
a. the de novo lipogenesis,
b. the glycerol 3-phosphate synthesis,
c. the gluconeogenesis from glycerol,
d. synthesis or burning of visceral fat and other segmental fat masses of a body segment,
e. building or wasting of segmental muscle masses of a body segment,
f. the total energy expenditure, and
g. the physical activity energy expenditure.

Accordingly, the scope should be determined not by the embodiment illustrated, but by the appended claims and their legal equivalents.

I claim:

1. A method for dynamic indirect individualized measurement of a daily change of body composition vector, a daily utilized energy intake vector, a daily macronutrient oxidation vector, a daily resting metabolic rate, at least one of daily unknown energy losses and gains, a daily rate of endogenous lipolysis, a daily nitrogen excretion, and a daily gluconeogenesis from protein comprising:
at a computing device configured to measure and predict metrics associated with at least one of a hydration characteristic, a body composition characteristic, and an energy metabolism characteristic:
obtaining, by a sensor, daily serial measurements from a user, wherein the daily serial measurements comprise at least one of a macronutrient energy intake, a resting metabolic rate, a physical activity energy expenditure based on a user's movements, and a weight amount;
deriving and solving a mathematical equation to calculate said daily utilized energy intake vector if ingested daily carbohydrate intake, ingested daily fat intake, and at least one of ingested daily protein intake are available and if ingested daily carbohydrate intake, ingested daily fat intake, and ingested daily protein intake are not available, deriving a mathematical model and using a minimum variance estimation and prediction method and a measured indirectly calculated change of body composition vector that can comprise use of at least one of a reference and a nominal trajectory method to estimate a daily utilized energy intake vector;

deriving and solving mathematical equations with said daily utilized energy intake vector to calculate said daily macronutrient oxidation vector, said daily resting metabolic rate, at least one of a daily estimation of unknown forms of energy losses and gains, said daily rate of endogenous lipolysis, said daily nitrogen excretion, said daily gluconeogenesis from protein, a daily estimation of a correction factor for gluconeogenesis from amino acids, a daily gluconeogenesis from glycerol, a daily estimation of a correction factor for de novo lipogenesis, a daily rate of de novo lipogenesis, a glycerol 3-phosphate synthesis, and an energy needed for fat synthesis;

deriving and solving a mathematical model and using said minimum variance estimation and prediction method and said measured indirectly calculated change of body composition vector that can comprise use of at least one of a reference and a nominal trajectory method to obtain an estimated indirectly calculated change of body composition vector;

performing a stochastic identification of an indirectly calculated correction factor for de novo lipogenesis, an indirectly calculated correction factor for gluconeogenesis from amino acids, and an indirectly calculated correction factor for at least one of unidentified energy losses and gains;

performing a state space model identification to estimate said daily change of body composition vector, said daily utilized energy intake vector, a daily macronutrient oxidation vector, said daily resting metabolic rate, at least one of daily unknown energy losses and gains, said daily rate of endogenous lipolysis, said daily nitrogen excretion, and said daily gluconeogenesis from protein;

in response to performing the stochastic and state space model identifications, updating a self correcting model of a utilized energy intake and a self adaptive model of the energy metabolism characteristic of a user;

generating an individualized metric and trend derived from the self correcting model and the self adaptive model regarding the at least one of the hydration characteristic, the body composition characteristic, and the energy metabolism characteristic of the user; and presenting the individualized metric and trend to the user via the computing device, whereby the individualized metric and trend provides improved predictive health information to the user for use to manage at least one of a user's health, fitness goals, body composition goals, hydration goals, and energy expenditure goals.

2. The method of claim 1, wherein performing the state space model identification comprises a state space model structure comprising:

a process model made up of matrix equation wherein said daily utilized energy intake vector is equal to the sum of a previous day's dynamic transition matrix multiplied with a previous day's utilized energy intake vector, plus a previous day's dynamic coupling matrix multiplied with said daily indirectly calculated change of body composition vector, plus a previous day's time varying bias vector; and a measurement model made up of a matrix equation wherein said daily utilized energy intake vector is equal to a product of an inverse matrix of the time varying utilized energy intake coupling matrix in at least one of a Retained and Released Energy Model of the Human Energy Metabolism and an energy constant matrix of the at least one of Retained and Released Energy Model of the Human Energy Metabolism and said daily indirectly calculated change of body composition vector minus the product of said inverse matrix of the time varying utilized energy intake coupling matrix in the at least one of Retained and Released Energy Model of the Human Energy Metabolism and an indirectly calculated bias vector of the at least one of Retained and Released Energy Model of the Human Energy Metabolism.

3. The method of claim 1, wherein the mathematical model equations for calculating dynamic indirect individualized measurements further comprises a measurement model of the macronutrient oxidation vector by deriving and solving a system of three linear equations for a rate of carbohydrate oxidation, a rate of fat oxidation, and a rate of protein oxidation wherein the first equation sets the constraint that a total energy expenditure equates to the sum of said rate of carbohydrate oxidation, plus said rate of fat oxidation, plus said rate of protein oxidation, plus an estimation of at least one of unknown energy losses and gains;

the second equation sets the constraint that said total energy expenditure equals the sum of an energy production calculated with known heat equivalent of oxygen for carbohydrate, plus an energy production calculated with known heat equivalent of oxygen for fat, plus an energy production calculated with known heat equivalent of oxygen for protein, plus said estimation of the at least one of unknown energy losses and gains; and the third equation sets the constraint that said energy production calculated with known heat equivalent of oxygen for protein equals six point twenty five times the energy density of protein times said daily nitrogen excretion minus said daily gluconeogenesis from protein.

4. The method of claim 1, wherein the mathematical model equations for calculating dynamic indirect individualized measurements further comprises modeling said daily resting metabolic rate by deriving and solving at least one of an equation for said daily resting metabolic rate with a filtering formula by adding up a time-varying constant energy expenditure plus a part of the resting metabolic rate which is independent of the body composition changes and the time-varying constant energy expenditure plus a synthesis cost of glycogen multiplied by a change of glycogen store on the previous day plus a synthesis cost of fat multiplied by a change of fat store on the previous day, plus a synthesis cost of protein multiplied by a change of protein store on the previous day and by deriving and solving an equation for said daily resting metabolic rate with a predictive formula by adding up said time-varying constant energy expenditure plus said part of the resting metabolic rate which is independent of the body composition changes and the time-varying constant energy expenditure plus the synthesis cost of glycogen multiplied by the change of glycogen store on a same day, plus the synthesis cost of fat multiplied by the change of fat store on the same day, plus the synthesis cost of proteins multiplied by the change of protein store on the same day.

5. The method of claim 4, wherein the modeling of the daily resting metabolic rate further comprises at least one of the filtering formula and the predictive formula, wherein said daily time-varying constant energy expenditure is estimated with said minimum variance estimation and prediction method and a directly measured resting metabolic rate from a calibration day.

6. The method of claim 1, wherein the mathematical model estimating said indirectly calculated change of body composition vector further comprises a state space model structure comprising:
a process model containing three linear equations wherein the first equation equates a daily energy of a glycogen store change with a sum of said daily utilized carbohydrate intake, plus said daily estimation of the correction factor for gluconeogenesis from amino acids multiplied by said daily gluconeogenesis from protein, plus said daily gluconeogenesis from glycerol, minus said daily estimation of the correction factor for de novo lipogenesis multiplied by said daily rate of de novo lipogenesis, minus said glycerol 3-phosphate synthesis, minus said energy needed for fat synthesis, minus said daily calculated rate of carbohydrate oxidation, minus said daily estimation of the at least one of unknown energy losses and gains, the second equation equates a daily energy of fat store change with a molecular weight ratio of free fatty acid to triglyceride multiplied with said daily utilized fat intake, plus said daily estimation of the correction factor for de novo lipogenesis multiplied by said daily rate of de novo lipogenesis, plus a molecular weight ratio glycerol to triglyceride multiplied with a daily change of the fat store, minus said daily calculated rate of fat oxidation, the third equation equates a daily energy of protein store change with said daily utilized protein intake, minus said daily estimation of the correction factor for gluconeogenesis from amino acids multiplied by said daily gluconeogenesis from protein, minus said daily calculated rate of protein oxidation;
a measurement model comprising a matrix equation wherein said daily indirectly calculated change of body composition vector equates with at least one of a matrix product of an inverse of a constant matrix of a Measurement Model of Body Composition Change from Lean-Fat-Protein and a change of an indirectly calculated Lean-Fat-Protein vector and a matrix equation wherein said daily indirectly calculated change of body composition vector equates with a matrix product of the inverse of a constant matrix of a Measurement Model of Body Composition Change from Lean-Fat-Resting-Metabolic-Rate and a daily change of the indirectly calculated Lean-Fat-Resting-Metabolic-Rate vector; and
a measurement model at least one of said change of indirectly calculated Lean-Fat-Protein vector, where said change of Lean-Fat-Protein vector is constructed from a daily change of indirectly measured lean body mass measured by a machine for detecting the resistance of a human subject at an extrapolated zero and infinite frequency, from a daily change of indirectly measured body fat mass measured by said machine, and from said daily energy of protein store change, and of said change of indirectly calculated Lean-Fat-Resting-Metabolic-Rate vector, where said Lean-Fat-Resting-Metabolic-Rate vector is constructed from said daily change of indirectly measured lean body mass measured by said machine, from said daily change of indirectly measured body fat mass measured by said machine, and from a daily resting metabolic rate with a filtering formula minus an indirectly calculated time-varying constant energy expenditure minus a part of the resting metabolic rate which is independent of a body composition changes and a time-varying constant energy expenditure.

7. The method of claim 6, further comprising using a daily indirectly calculated correction factor for de novo lipogenesis, a daily indirectly calculated correction factor for gluconeogenesis from amino acids, and a daily indirectly calculated correction factor for at least one of unknown energy losses and gains to estimate with said minimum variance estimation and prediction method said daily estimated correction factor for de novo lipogenesis, said daily estimated correction factor for gluconeogenesis from amino acids, and said daily estimated correction factor for the at least one of unknown energy losses and gains.

8. The method of claim 1, wherein the mathematical model equations for calculating dynamic indirect individualized measurements further comprises deriving and solving a linear invertible equation for said daily endogenous lipolysis by adding up a product of a daily fat store dependent coefficient for rate of endogenous lipolysis and a daily body fat mass, plus a product of a carbohydrate intake dependent coefficient for rate of endogenous lipolysis and a utilized carbohydrate intake, plus a daily bias for rate of endogenous lipolysis.

9. The method of claim 8, wherein the linear invertible equation for said daily endogenous lipolysis further comprises deriving and solving an equation for an estimated rate of endogenous lipolysis with calibration by multiplying said rate of endogenous lipolysis with said estimation of a correction factor for de novo lipogenesis and a new value for a baseline lipolysis rate after calibration and dividing the multiplication of said rate of endogenous lipolysis with said estimation of the correction factor for de novo lipogenesis and the new value for the baseline lipolysis rate after calibration by a baseline lipolysis rate before calibration.

10. The method of claim 1, wherein the mathematical model equations for calculating dynamic indirect individualized measurements further comprises deriving and solving an equation for said daily nitrogen excretion by first subtracting a product of the energy density of protein with a previous day's change of protein store from said daily protein intake, then dividing a resulting value by six point twenty five times the energy density of protein.

11. The method of claim 1, wherein the mathematical model equations for calculating dynamic indirect individualized measurements further comprises deriving and solving a linear invertible equation for daily gluconeogenesis from protein by adding up a protein store dependent coefficient for gluconeogenesis from protein multiplied by a protein mass, plus a carbohydrate intake dependent coefficient for gluconeogenesis from protein multiplied by said utilized carbohydrate intake plus a protein intake dependent coefficient for gluconeogenesis from protein multiplied by said utilized protein intake, plus a bias for gluconeogenesis from protein.

12. The method of claim 11, wherein the modeling of the daily gluconeogenesis from protein further comprises an estimated gluconeogenesis from protein with calibration by deriving and solving an equation multiplying said gluconeogenesis from protein with an estimation of said correction factor for gluconeogenesis from amino acids and a new value for a basal gluconeogenesis rate after calibration and dividing the multiplication of said gluconeogenesis from protein with the estimation of said correction factor for gluconeogenesis from amino acids and the new value for the basal gluconeogenesis rate after calibration by the basal gluconeogenesis rate.

13. The method of claim 1, wherein the self correcting model of the utilized energy intake comprises of estimating a daily utilized energy of carbohydrate, a fat, and a protein caloric intake.

14. The method of claim 1, wherein the self adaptive model of the energy metabolism characteristic comprises of estimating a daily change of body composition, comprising a change of glycogen store, a fat store, and a protein store.

* * * * *